US007728106B2

(12) United States Patent
Wang

(10) Patent No.: US 7,728,106 B2
(45) Date of Patent: Jun. 1, 2010

(54) HIV-1 GLYCOPEPTIDES AND DERIVATIVES; PREPARATION AND APPLICATIONS THEREOF

(75) Inventor: Lai-Xi Wang, Ellicott City, MD (US)

(73) Assignee: University of Maryland Biotechnology Institute, Baltimore, MD (US)

( * ) Notice: Subject to any disclaimer, the term of this patent is extended or adjusted under 35 U.S.C. 154(b) by 721 days.

(21) Appl. No.: 11/479,701

(22) Filed: Jun. 30, 2006

(65) Prior Publication Data

US 2007/0224211 A1 Sep. 27, 2007

Related U.S. Application Data

(60) Provisional application No. 60/696,177, filed on Jul. 1, 2005.

(51) Int. Cl.
*C07K 14/16* (2006.01)
*C07K 1/113* (2006.01)

(52) U.S. Cl. ....................... 530/324; 530/333; 530/345; 530/395

(58) Field of Classification Search ....................... None
See application file for complete search history.

(56) References Cited

FOREIGN PATENT DOCUMENTS

WO WO-2004/03366 A2 4/2004

OTHER PUBLICATIONS

GenBank: K03455.1.*

Galanakis et al. ("Conformational Properties of HIV-1 gp120/V3 Immunogenic Domains," Curr. Med. Chem., 2005, 12, 1551-1568).*

GenBank K03455.1 "Human immunodeficiency virus type 1 (HXB2), complete genome; HIV1/HTLV-III/LAV reference genome" Oct. 21, 2002.*

K. S. Cole et al.; Removal of N-linked glycosylation sites in the V1 region of simian immunodeficiency virus gp120 results in redirection of B-cell responses to V3; J Virol; 2004; 78:1525-1539.

R. Pantophlet et al.; Immunofocusing: antigen engineering to promote the induction of HIV-neutralizing antibodies; Trends Mol Med; 2003; 9:468-473.

S. E. O'Connor et al.; Modulation of protein structure and function by asparagine-linked glycosylation; Chem Biol; 1996; 3:803-812.

B. Imperiali et al.; Effect of N-linked glycosylation on glycopeptide and glycoprotein structure; Curr. Opin. Chem. Biol.; 1999; 3:643-649.

B. Imperiali et al.; Asparagine-linked glycosylation: speficity and function of oligosaccharyl transferase; Bioorg Med Chem; 1995; 3:1565-1578.

A. H. Andreotti et al.; Effects of glycosylation on peptide backbone conformation; J. Am. Chem. Soc.; 1993; 115:3352-3353.

R. Liang et al.; Sensitivity of glycopeptide conformation to carbohydrate chain length; J. Am. Chem. Soc.;1995; 117:10395-10396.

S. E. O'Connor et al.; A molecular basis for glycosylation-induced conformational switching; Chem Biol; 1998; 5:427-437.

S. E. O'Connor et al.; Probing the effect of the outer saccharide residues of N-linked glycans on peptide conformation; J Am Chem Soc; 2001; 123:6187-6188.

C. J. Bosques et al.; Effects of glycosylation on peptide conformation: a synergistic experimental and computational study; J Am Chem Soc; 2004; 126:8421-8425.

W. F. Vranken et al.; Conformational features of a synthetic cyclic peptide corresponding to the complete V3 loop of the RF HIV-1 strain in water and water/trifluoroethanol solutions; Eur J Biochem; 1996; 236:100-108.

W. F. Vranken et al.; Conformational model for the consensus V3 loop of the envelope protein gp120 of HIV-1 in a 20% trifluoroethanol/water solution; Eur J Biochem; 2001; 268:2620-2628.

W. F. Vranken et al.; The complete Consensus V3 loop peptide of the envelope protein gp120 of HIV-1 shows pronounced helical character in solution; FEBS Lett; 1995; 374:117-121.

P. Catasti et al.; Structure and polymorphism of HIV-1 third variable loops; J Biol Chem; 1996; 271:8236-8242.

P. Catasti et al.; Local and global structural properties of the HIV-MN V3 loop; J Biol Chem; 1995; 270:2224-2232.

J. B. Ghiara et al.; Structure-based design of a constrained peptide mimic of the HIV-1 V3 loop neutralization site; J Mol Biol; 1997; 266:31-39.

A. Zvi et al.; Conformation of the principal neutralizing determinant of human immunodeficiency virus type 1 in complex with an anti-gp120 virus neutralizing antibody studied by two-dimensional nuclear magnetic resonance difference spectroscopy; Biochemistry; 1997; 36:8619-8627.

E. Cabezas et al.; A structure-based approach to a synthetic vaccine for HIV-1; Biochemistry; 2000; 39:14377-14391.

J. M. Rini et al.; Crystal structure of a human immunodeficiency virus type 1 neutralizing antibody, 50.1, in complex with its V3 loop peptide antigen; Proc Natl Acad Sci; 1993; 90:6325-6329 U S A.

J. B. Ghiara et al.; Crystal structure of the principal neutralization site of HIV-1; Science; 1994; 264:82-85.

R. L. Stanfield et al.; Recurring conformation of the human immunodeficiency virus type 1 gp120 V3 loop; Virology; 2003; 315:159-173.

R. L. Stanfield et al.; Structural rationale for the brand neutralization of HIV-1 by human monoclonal antibody 447-52D; Structure (Camb); 2004; 12:193-204.

(Continued)

*Primary Examiner*—Anish Gupta
*Assistant Examiner*—Christina Bradley
(74) *Attorney, Agent, or Firm*—Marianne Fuierer; Moore & Van Allen, PLLC

(57) ABSTRACT

A method of making a synthetic glycopeptide, by addition of a synthetic oligosaccharide oxazoline to a GlcNAc-containing peptide precursor in the presence of an enzyme selected from among Endo-A and Endo-M. In a specific implementation, the method is utilized to synthesize a trivalent V3-domain glycopeptide including three V3-domain glycopeptides on a scaffold, wherein the three V3-domain glycopeptides are arranged to mimic the V3 domain presentation in trimeric gp120. Such trivalent V3-domain glycopeptides can be utilized in a vaccine for the treatment or prevention of HIV-1 infection.

11 Claims, 9 Drawing Sheets

OTHER PUBLICATIONS

I. Laczko et al.; Synthesis and conformational studies of N-glycosylated analogues of the HIV-1 prinicipal neutralizing determinant; Biochemistry; 1992; 31:4282-4288.

X. Huang et al.; Structural comparison of a 15 residue peptide from the V3 loop of HIV- 1IIIb and an O-glycosylated analogue; FEBS Lett; 1996; 393:280-286.

X. Huang et al.; Glycosylation affects both the three-dimensional structure and antibody binding properties of the HIV-1IIIB GP120 peptide RP135; Biochemistry; 1997; 36:10846-10856.

B. Chen et al.; Structure of an unliganded simian immunodeficiency virus gp120 core; Nature; 2005; 433:834-841.

B. Chen et al.; Determining the structure of an unliganded and fully glycosylated SIV gp120 envelope glycoprotein; Structure (Camb); 2005; 13:197-211.

P. D. Kwong et al.; Structure of an HIV gp120 envelope glycoprotein in complex with the CD4 receptor and a neutralizing human antibody; Nature; 1998; 393:648-659.

O. Hartley et al.; V3: HIV's switch-hitter; AIDS Res Hum Retroviruses; 2005; 21:171-189.

M. K. Gorny et al.; Neutralization of diverse human immunodeficiency virus type 1 variants by an anti-V3 human monoclonal antibody; J Virol; 1992; 66:7538-7542.

A. J. Conley et al.; Neutralization of primary human immunodeficiency virus type 1 isolates by the broadly reactive anti-V3 monoclonal antibody, 447-52D; J Virol; 1994; 68:6994-7000.

C. P. Krachmarov et al.; V3-specific polyclonal antibodies affinity purified from sera of infected humans effectively neutralize primary isolates of human immunodeficiency virus type 1; AIDS Res Hum Retroviruses; 2001; 17:1737-1748.

S. Zolla-Pazner et al.; The Cross-Clade Neutralizing Activity of a Human Monoclonal Antibody Is Determined by the GPGR V3 Motif of HIV Type 1; AIDS Res Hum Retroviruses; 2004; 20:1254-1258.

M. E. White-Scharf et al.; Broadly neutralizing monoclonal antibodies to the V3 region of HIV-1 can be elicited by peptide immunization; Virology; 1993; 192:197-206.

M. K. Gorny et al.; The v3 loop is accessible on the surface of most human immunodeficiency virus type 1 primary isolates and serves as a neutralization epitope; J Virol; 2004; 78:2394-2404.

P. D. Kwong et al.; Oligomeric modeling and electrostatic analysis of the gp120 envelope glycoprotein of human immunodeficiency virus; J Virol; 2000; 74:1961-1972.

G. J. LaRosa et al.; Conserved sequence and structural elements in the HIV-1 principal neutralizing determinant; Science; 1990; 249:932-935.

T. L. Hoffman et al.; HIV-1 envelope determinants for cell tropism and chemokine receptor use; Mol Membr Biol; 1999; 16:57-65.

C. D. Rizzuto et al.; A conserved HIV gp120 glycoprotein structure involved in chemokine receptor binding; Science; 1998; 280:1949-1953.

C. Rizzuto et al.; Fine definition of a conserved CCR5-binding region on the human immunodeficiency virus type 1 glycoprotein 120; AIDS Res Hum Retroviruses; 2000; 16:741-749.

S. Basmaciogullari et al.; Identification of conserved and variable structures in the human immunodeficiency virus gp120 glycoprotein of importance for CXCR4 binding; J Virol; 2002; 76:10791-10800.

M. Sharon et al.; Alternative conformations of HIV-1 V3 loops mimic beta hairpins in chemokines, suggesting a mechanism for coreceptor selectivity; Structure (Camb); 2003; 11:225-236.

A. Yonezawa et al.; Replacement of the V3 region of gp120 with SDF-1 preserves the infectivity of T-cell line-tropic human immunodeficiency virus type 1; J Virol; 2001; 75:4528-4267.

B. Nardelli et al.; A chemically defined synthetic vaccine model for HIV-1; J Immunol; 1992; 148:914-920.

H. X. Liao et al.; Induction of antibodies in guinea pigs and rhesus monkeys against the human immunodeficiency virus type 1 envelope: neutralization of nonpathogenic and pathogenic primary isolate simian/human immunodeficiency virus strains; J Virol; 2000; 74:254-263.

A. Rubinstein et al.; Immunologic responses of HIV-1-infected study subjects to immunization with a mixture of peptide protein derivative-V3 loop peptide conjugates; J Acquir Immune Defic Syndr; 1999; 22:467-476.

H. Tian et al.; HIV epitope-peptides in aluminum adjuvant induced high levels of epitope-specific antibodies; Int Immunopharmacol; 2001; 1:763-768.

L. X. Wang et al.; Binding of high-mannose-type oligosaccharides and synthetic oligomannose clusters to human antibody 2G12: implications for HIV-1 vaccine design; Chem Biol; 2004; 11:127-134.

H. Li et al.; Design and synthesis of a template-assembled oligomannose cluster as an epitope mimic for human HIV-neutralizing antibody 2G12; Org Biomol Chem; 2004; 2:483-488.

V. Kudryashov et al.; Toward optimized carbohydrate-based anticancer vaccines: epitope clustering, carrier structure, and adjuvant all influence antibody responses to Lewis(y) conjugates in mice; Proc Natl Acad Sci; 2001; 98:3264-3269; U S A.

G. Arsequell et al.; Recent advances in the synthesis of complex N-glycopeptides; Tetrahedron: Asymmetry; 1999; 10:3045-3094.

M. Meldal et al.; Synthetic methods of glycopeptide assembly, and biological analysis of glycopeptide products; Curr. Opin. Chem. Biol.; 1997; 1:552-563.

M. Meldal et al.; A general approach to the synthesis of O- and N-linked glycopeptides; Glycoconjugate J.; 1994; 11:59-63.

M. J. Grogan et al.; Homogeneous glycopeptides and glycoproteins for biological investigation; Annu. Rev. Biochem.; 2002; 71:593-634.

P. Sears et al.; Toward automated synthesis of oligosaccharides and glycoproteins; Science; 2001; 291:2344-2350.

K. Yamamoto; Chemoenzymatic synthesis of bioactive glycopeptide using microbial endoglycosidase; J. Biosci. Bioeng; 2001; 92:493-501.

L. X. Wang et al.; Synthesis of bioactive glycopeptides through endoglycosidase-catalyzed transglycosylation, p. 73-92; In P. G. Wang and Y. Ichikawa (ed.), Synthesis of Carbohydrates through Biotechnology. American Chemical Society, 2004; Washington, D.C.

L. X. Wang et al.; Combined chemical and enzymic synthesis of a C-glycopeptide and its inhibitory activity toward glycoamidases; J. Am. Chem. Soc.; 1997; 119:11137-11146.

M. Mizuno et al.; Synthesis of a glycopeptide containing oligosaccharides: chemoenzymatic synthesis of eel calcitonin analogues having natural N-linked oligosaccharides; J. Am. Chem. Soc.; 1999; 121:284-290.

L. X. Wang et al.; Chemoenzymatic synthesis of a high-mannose type N-glycopeptide analog with C-glycosidic linkage; Tetrahedron Lett.; 1996; 37:1975-1978.

K. Takegawa et al.; Enzymatic synthesis of a neoglycoconjugate by transglycosylation with Arthrobacter endo-beta-N-acetylglucosaminidase: a substrate for colorimetric detection of endo-beta-N-acetylglucosaminidase activity; Anal. Biochem.; 1998; 257:218-223.

S. Singh et al.; Chemoenzymatic synthesis of high-mannose type HIV-1 gp120 glycopeptides; Bioorg Med Chem Lett; 2003; 13:327-330.

H. Li et al.; Chemoenzymatic synthesis of CD52 glycoproteins carrying native N-glycans; Bioorg Med Chem Lett; 2005; 15:895-898.

L. X. Wang et al.; Chemoenzymatic synthesis of HIV-1 glycopeptides; Effects of glycosylation on the antiviral activity and alpha-helix bundle-forming ability of gp41 peptide C34; 2005; ChemBioChem in press.

A. Seko et al.; Occurence of a sialylglycopeptide and free sialylglycans in hen's egg yolk; Biochim Biophys Acta; 1997; 1335:23-32.

J. Q. Fan et al.; Enhanced transglycosylation activity of Arthrobacter protophormiae endo- beta-N-acetylglucosaminidase in media containing organic solvents; J. Biol. Chem.; 1995; 270:17723-17729.

X. Geng et al.; In Pursuit of Carbohydrate-Based HIV Vaccines, Part 2: The Total Synthesis of High-Mannose-Type gp120 Fragments-Evaluation of Strategies Directed to Maximal Convergence; Angew Chem Int Ed; 2004; 43:2562-2565.

M. Mandal et al.; In Pursuit of Carbohydrate-Based HIV Vaccines, Part 1: The Total Synthesis of Hybrid-Type gp120 Fragments; Angew Chem Int Ed; 2004; 43:2557-2561.
K. K. Chittur; FTIR/ATR for protein adsorption to biomaterial surfaces; Biomaterials; 1998; 19:357-369.
C. Vigano et al.; Attenuated total reflection IR spectroscopy as a tool to investigate the structure, orientation and tertiary structure changes in peptides and membrane proteins; Biopolymers; 2000; 55:373-380.
Y. Morikawa et al.; Legitimate and illegitimate cleavage of human immunodeficiency virus glycoproteins by furin; J Virol; 1993; 67:3601-3604.
N. Brakch et al.; Structural investigation and kinetic characterization of potential cleavage sites of HIV GP160 by human furin and PC1; Biochem Biophys Res Commun; 1995; 213:356-361.
F. Vollenweider et al.; Comparative cellular processing of the human immunodeficiency virus (HIV-1) envelope glycoprotein gp160 by the mammalian subtilisin/kexin-like convertases; Biochem J; 1996; 314:521-532.
H. Geyer et al.; Carbohydrates of human immunodeficiency virus. Structures of oligosaccharides linked to the envelope glycoprotein 120; J Biol Chem; 1988; 263:11760-11767.
J. Ni et al.; Synthesis, conformation, and immunogenicity of monosaccharide-centerd multivalent HIV-1 gp41 peptides containing the sequence of DP178; Bioorg Med Chem; 2004; 12:3141-3148.
J. P. Tam; Recent advances in multiple antigen peptides; J. Immunol. Methods; 1996; 196:17-32.
L. X. Wang et al.; Carbohydrate-centered maleimide cluster as new types of templates for multivalent peptide assembling: Synthesis of multivalent HIV-1 gp41 peptides; Bioorg. Med. Chem.; 2003; 11:129-136.
J. Ni et al.; Synthesis of maleimide-activated carbohydrates as chemoselective tags for site-specific glycosylation of peptides and proteins; Bioconjug Chem; 2003; 14:232-238.
H.Li et al.; Cholic acid as template for multivalent peptide assembly; Org Biomol Chem; 2003; 1:3507-3513.
K. P. Naicker et al.; Design and synthesis of alpha Gal-conjugated peptide T20 as novel antiviral agent for HIV-immunotargeting; Org Biomol Chem; 2004; 2:660-664.
H. Li et al.; Synthetic bivalent CD4-mimetic miniproteins show enhanced anti-HIV activity over the monovalent miniprotein; Bioconjug Chem; 2004; 15:783-789.
J. Shao et al.; Unprotected peptides as building blocks for the synthesis of peptide dendrimers with oxime, hydrazone, and thiazolidine linkages; J. Am. Chem. Soc.; 1995; 117:3893-3899.
K. Rose; Facile synthesis of homogeneous artificial proteins; J. Am. Chem. Soc.; 1994; 116:30-33.
K. Rose et al.; A synthetic peptide-based polyoxime vaccine construct of high purity and activity; Mol Immunol; 1995; 32:1031-1037.
Dudkin, Vadim Y., et al., Toward Fully Synthetic Carbohydrate-Based HIV Antigen Design: On the Critical Role of Bivalency, J. Am. Chem. Soc., Aug. 11, 2004, pp. 9560-9562, vol. 126, No. 31.
Li, Bing, et al., Highly Efficient Endoglycosidase-Catalyzed Synthesis of Glycopeptides Using Oligosaccharide Oxazolines as Donor . . . , J. Am. Chem. Soc., Jul. 13, 2005, pp. 9692-9693, vol. 127, No. 27.
Li, Hengguang, et al., Design and synthesis of a template-assembled oligomannose cluster as an epitope mimic for human HIV-neutralizing . . . , Org. Biomol. Chem., 2004, pp. 483-488, vol. 2, No. 4.
Li, Hengguang, et al., Chemoenzymatic Synthesis of HIV-1 V3 Glycopeptides Carrying Two N-Glycans and Effects of Glycosylation on the Peptide . . . , J. Org. Chem., Nov. 25, 2005, pp. 9990-9996, vol. 70, No. 24.
Zolla-Pazner, Susan, Identifying epitopes of HIV-1 that induce protective antibodies, Nature Reviews Immunology, Mar. 2004, pp. 199-210, vol. 4, No. 3.
K. Rose et al.; Natural peptides as building blocks for the synthesis of large protein-like molecules with hydrazone and oxime linkages; Bioconjug Chem; 1996; 7:552-556.
E. H. Nardin et al.; Plasmodium falciparum polyoximes: highly immunogenic synthetic vaccines constructed by chemoselective ligation of repeat B-cell epitopes and a universal T-cell epitope of CS protein; Vaccine; 1998; 16:590-600.
W. Zheng et al.; Totally synthetic lipid-containing polyoxime peptide constructs are potent immunogens; Vaccine; 2000; 18:1031-1039.
J. Chen et al.; A novel method for the rational construction of well-defined immunogens: the use of oximation to conjugate cholera toxin B subunit to a peptide-polyoxime complex; Bioconjug Chem; 2003; 14:614-618.
G. Wu et al.; The binding of a glycoprotein 120 V3 loop peptide to HIV-1 neutralizing antibodies. Structural implications; J Biol Chem; 2000; 275:36645-36652.
E. Coeffier et al.; Antigenicity and immunogenicity of the HIV-1 gp41 epitope ELDKWA inserted into permissive sites of the MalE protein; Vaccine; 2001; 19:684-693.
V. Y. Dudkin et al.; Toward fully synthetic carbohydrate-based HIV antigen design: on the critical role of bivalency; J Am Chem Soc; 2004; 126:9560-9562.
T. Fouts et al.; Crosslinked HIV-1 envelope-CD4 receptor complexes elicit broadly cross- reactive neutralizing antibodies in rhesus macaques; Proc Natl Acad Sci; 2002; 99:11842-11847, U S A.
A. DeVico et al.; Covalently crosslinked complexes of human immunodeficiency virus type 1 (HIV-1) gp120 and CD4 receptor elicit a neutralizing immune response that includes antibodies selective for primary virus isolates; Virology; 1996; 218:258-263.
T. Vogel et al.; The majority of neutralizing Abs in HIV-1-infected patients recognize linear V4 loop sequences. Studies using HIV-1MN multiple antigenic peptides; J Immunol; 1994; 153:1895-1904.
D. A. Johnson et al.; Synthesis and biological evaluation of a new class of vaccine adjuvants: aminoalkyl glucosaminide 4-phosphates (AGPs); Bioorg Med Chem Lett; 1999; 9:2273-2278.
J. C. Griffiths et al.; Induction of high-titer neutralizing antibodies, using hybrid human immunodeficiency virus V3-Ty viruslike particles in a clinically relevant adjuvant; J Virol; 1991; 65:450-456.
N. E. Raya et al.; A prime-boost regime that combines Montanide ISA720 and Alhydrogel to induce antibodies against the HIV-1 derived multiepitope polypeptide TAB9; Vaccine; 1999; 17:2646-2650.
J. Goudsmit et al.; Human immunodeficiency virus type 1 neutralization epitope with conserved architecture elicits early type-specific antibodies in experimentally infected chimpanzees; Proc Natl Acad Sci; 1998; U S A 85:4478-4482.
J. S. Andris et al.; Molecular characterization of five human anti-human immunodeficiency virus type 1 antibody heavy chains reveals extensive somatic mutation typical of an antigen-driven immune response; Proc Natl Acad Sci; 1991; 88:7783-7787, U S A.
A. L. DeVico et al.; Monoclonal antibodies raised against covalently crosslinked complexes of human immunodeficiency virus type 1 gp120 and CD4 receptor identify a novel complex-dependent epitope on gp 120; Virology; 1995; 211:583-588.
J. M. Burns et al.; A new monoclonal antibody, mAb 4A12, identifies a role for the glycosaminoglycan (GAG) binding domain of RANTES in the antiviral effect against HIV-1 and intracellular Ca2+ signaling; J Exp Med; 1998; 188:1917-1927.
E. S. Daar et al.; High concentrations of recombinant soluble CD4 are required to neutralize primary human immunodeficiency virus type 1 isolates; Proc. Natl. Acad. Sci.; 1990; 87:6574-6578; U. S. A.
R. I. Connor et al.; Change in coreceptor use correlates with disease progression in HIV-1—infected individuals; J. Exp. Med.; 1997; 185:621-628.
R. I. Conner et al.; Increased viral burden and cytopathicity correlate temporally with CD4+ T-lymphocyte decline and clinical progression in human immunodeficiency virus type 1-infected individuals; J. Virol.; 1993; 67:1772-1777.
O. Werdelin et al.; Processing of glycans on glycoprotein and glycopeptide antigens in antigen-presenting cells; Proc Natl Acad Sci; 2002; 99:9611-9613; U S A.
D. Zhou et al.; Lysosomal glycosphingolipid recognition by NKT cells; Science; 2004; 306:1786-1789.
D.R. Burton et al.; HIV vaccine design and the neutralizing antibody problem; Nat Immunol; 2004; 5:233-236.
S. Zolla-Pazner; identifying epitopes of HIV-1 that induce protective antibodies; Nat Rev Immunol; 2004; 4:199-210.
R. Wyatt et al.; The antigenic structure of the HIV gp120 envelope glycoprotein; Nature; 1998; 393:705-711.

A. Trkola et al.; Human monoclonal antibody 2G12 defines a distinctive neutralization epitope on the gp120 glycoprotein of human immunodeficiency virus type 1; J Virol; 1996; 70:1100-1108.
C. N. Scanlan et al.; The broadly neutralizing anti-human immunodeficiency virus type 1 antibody 2G12 recognizes a cluster of alpha1—>2mannose residues on the outer face of gp120; J Virol; 2002; 76:7306-7321.
R. W. Sanders et al., The mannose-dependent epitope for neutralizing antibody 2G12 on human immunodeficiency virus type 1 glycoprotein gp120; J Virol; 2002; 76:7293-7305.
S. J. Danishefsky et al.; From the Laboratory to the Clinic: A Retrospective on Fully Synthetic Carbohydrate-Based Anticancer Vaccines Frequently used abbreviations are listed in the appendix; Angew Chem Int Ed; 2000 39:836-863.
B. Imperiali et al.; Conformational implications of asparagine-linked glycosylation; Proc Natl Acad Sci; 1995; 92:97-101; U S A.
E. Lisowska; The role of glycosylation in protein antigenic properties; Cell Mol Life Sci; 2002; 59:445-455.
R.Pantophlet et al.; Hyperglycosylated mutants of human immunodeficiency virus (HIV) type 1 monomeric gp120 as novel antigens for HIV vaccine design; J Virol; 2003; 77:5889-5901.
R. R. Garrity et al.;, Refocusing neutralizing antibody response by targeted dampening of an immunodominant epitope; J Immunol; 1997; 159:279-289.
G. J. Nabel; Challenges and opportunities for development of an AIDS vaccine; Nature; 2001; 410:1002-1007.
A. J.McMichael et al.; Cellular immune responses to HIV; Nature; 2001; 410:980-987.
D. R. Burton; Antibodies, viruses and vaccines; Nat Rev Immunol; 2002; 2:706-713.
E. A. Emini et al.; Prevention of HIV-1 infection in chimpanzees by gp120 V3 domain-specific monoclonal antibody; Nature; 1992; 355:728-730.
R. Shibata et al.; Neutralizing antibody directed against the HIV-1 envelope glycoprotein can completely block HIV-1/SIV chimeric virus infections of macaque monkeys; Nat Med; 1999, 5:204-210.
J. R. Mascola et al.; Protection of macaques against vaginal transmission of a pathogenic HIV- 1/SIV chimeric virus by passive infusion of neutralizing antibodies; Nat Med; 2000; 6:207-210.
T. W. Baba et al.; Human neutralizing monoclonal antibodies of the IgG1 subtype protect against mucosal simian-human immunodeficiency virus infection; Nat Med; 2000; 6:200-206.
P. W. Parren et al.; Antibody protects macaques against vaginal challenge with a pathogenic R5 simian/human immunodeficiency virus at serum levels gving complete neutralization in vitro; J Virol; 2001; 75:8340-8347.
D. C. Chan et al.; Core structure of gp41 from the HIV envelope glycoprotein; Cell; 1997; 89:263-273.
D. C. Chan et al.; HIV entry and its inhibition; Cell; 1998; 93:681-684.
E. O. Saphire et al.; Crystal structure of a neutralizing human IGG against HIV-1: a template for vaccine design; Science; 2001; 293:1155-1159.
D. A. Calarese et al.; Antibody domain exchange is an immunological solution to carbohydrate cluster recognition; Science; 2003; 300:2065-2071.
C. E. Perker et al.; Fine definition of the epitope on the gp41 glycoprotein of human immunodeficiency virus type 1 for the neutralizing monoclonal antibody 2F5; J Virol; 2001; 75:10906-10911.
M. B. Zwick et al.; Broadly neutralizing antibodies targeted to the membrane-proximal external region of human immunodeficiency virus type 1 glycoprotein gp41; J Virol; 2001; 75:10892-10905.
G. Ofek et al.; Structure and mechanistic analysis of the anti-human immunodeficiency virus type 1 antibody 2F5 in complex with its gp41 eptitope; J Virol; 2004; 78:10724-10737.
M. K. Gorny et al.; Human monoclonal antibodies specific for conformation-sensitive epitopes of V3 neutralize human immunodeficiency virus type 1 primary isolates from various clades; J Virol; 2002; 76:9035-9045.
P. M. Rudd et al.; Glycosylation and the immune system; Science; 2001; 291:2370-2376.
A. Helenius et al.; Intracellular functions of N-linked glycans; Science; 2001; 291:2364-2369.
T. Mizuochi et al.; Diversity of oligosaccharide structures on the envelope glycoprotein gp 120 of human immunodeficiency virus 1 from the lymphoblasted cell line H9. Presence of complex-type oligosaccharides with bisecting N- acetylglucosamine residues; J Biol Chem; 1990; 265:8519-8524.
C. K. Leonard et al.; Assignment of intrachain disulfide bonds and characterization of potential glycosylation sites of the type 1 recombinant human immunodeficiency virus envelope gylcoprotein (gp120) expressed in Chinese hamster ovary cells; J Biol Chem; 1990; 265:10373-10382.
X. Zhu et al.; Mass spectrometric characterization of the glycosylation pattern of HIV- gp120 expressed in CHO cells; Biochemistry; 2000; 39:11194-11204.
C. Perrin et al.; Role of gp41 glycosylation sites in the biological activity of human immunodeficiency virus type 1 envelope glycoprotein; Virology; 1998; 242:338-345.
W. E. Johnson et al.; Conserved, N-linked carbohydrates of human immunodeficiency virus type 1 gp41 are largely dispensable for viral replication; J Virol; 2001; 75:11426-11436.
R. Kornfeld et al.; Assembly of asparagine-linked oligosaccharides; Annu Rev Biochem; 1985; 54:631-664.
J. N. Reitter et al.; A role for carbohydrates in immune evasion in AIDS; Nat Med; 1998; 4:679-684.
X. Wei et al.; Antibody neutralization and escape by HIV-1; Nature; 2003; 422:307-312.
N. K. Back et al.; An N-glycan within the human immunodeficiency virus type 1 gp120 V3 loop affects virus neutralization; Virology; 1994; 199:431-438.
A. Ly et al.; V2 loop glycosylation of the human immunodeficiency virus type 1 SF162 envelope facilitates interaction of this protein with CD4 and CCR5 receptors and protects the virus from neutralization by anti-V3 loop and anti-CD4 binding site antibodies; J Virol; 2000; 74:6769-6776.
M. Koch et al.; Structure-based targeted deglycosylation of HIV-1 gp120 and effects on neutralization sensitivity and antibody recognition; Virology; 2003; 313:387-400.
S. E. Malenbaum et al.; The N-terminal V3 loop glycan modulates the interaction of clade A and B human immunodeficiency virus type 1 envelopes with CD4 and chemokine receptors; J Virol; 2000; 74:11008-11016.
C. Grundner et al.; Factors limiting the immunogenicity of HIV-1 gp120 envelope glycoproteins; Virology; 2004 330:233-248.
R. A. McCaffrey et al.; N-linked glycosylation of the V3 loop and the immunologically silent face of gp120 protects human immunodeficiency virus type 1 SF162 from neutralization by anti-gp120 and anti-gp41 antibodies; J Virol; 2004 78:3279-3295.
S. M. Kang et al.; Modified HIV envelope proteins with enhanced binding to neutralizing monoclonal antibodies; Virology; 2005; 331:20-32.
M. I. Quinones-Kochs et al.; Role of N-linked glycans in a human immunodeficiency virus envelope glycoprotein: effects on protein function and the neutralizing antibody response; J Virol; 2002; 76:4199-4211.

* cited by examiner high-mannose type CD52 complex type CD52

M6-gp120(336-342)

gp41 Glyco-C34

| Analysis by K2d software | α-helix % | β -turn % | random coil % |
|---|---|---|---|
| V3 | 23 | 24 | 53 |
| V3-$G_2M_3$ | 22 | 27 | 51 |
| V3-$(G_2M_3)_2$ | 13 | 39 | 48 |

HB-V3-CT

HB-V3-HM

BAL-V3-CT

BAL-V3-HM

HIV-1 GLYCOPEPTIDES AND DERIVATIVES; PREPARATION AND APPLICATIONS THEREOF

CROSS-REFERENCE TO RELATED APPLICATION

The benefit of priority of U.S. Provisional Patent Application No. 60/696,177 filed Jul. 1, 2005 for "HIV-1 Glycopeptides and Derivatives; Preparation and Applications Thereof," is hereby claimed under the provisions of 35 USC §119. The disclosure of said U.S. Provisional Patent Application No. 60/696,177 is hereby incorporated herein by reference in its entirety, for all purposes.

STATEMENT OF GOVERNMENT RIGHTS

The United States Government has rights in this invention under Grant Nos. R21 AI051235 and R21 AI054354.

BACKGROUND OF THE INVENTION

1. Field of the Invention

The present invention relates to the synthesis of glycopeptides and uses thereof, and more particularly, to the novel synthesis of V3 glycopeptides and the use of same for in vivo immunogens that induce broadly neutralizing antibodies.

2. Background of the Related Art

The human immunodeficiency virus type 1 (HIV-1) is the retrovirus that caused the global epidemic of AIDS. Today, more than 40 million people are estimated to live with HIV/AIDS and the epidemic is still expanding [12]. There is no doubt that the best hope to stop the worldwide epidemic is an effective HIV-1 vaccine. To achieve a maximal protection, an effective HIV-1 vaccine may need to induce both humoral and cellular immunity [1, 2, 13-16]. While cytotoxic T lymphocytes (CTL) response is important to control and reduce HIV-1 infection by killing the infected cells [15], passive immunization experiments in various animal models have repeatedly demonstrated that neutralizing antibodies with appropriate specificity, when present in sufficient concentrations, can provide sterilizing immunity [17-21]. Therefore, the design of an immunogen that is able to induce broadly neutralizing antibodies remains a major goal in HIV-1 vaccine development.

The past two decades have witnessed tremendous advances in the understanding of the structure and function of the envelope glycoproteins in connection with their immunological properties [1, 3, 22, 23]. So far, a panel of neutralizing antibodies has been identified that are broadly reactive against HIV-1 primary isolates. These include monoclonal antibodies (mAbs) b12 and 2G12 that target discontinuous epitopes on gp120 [24, 25], and mAbs 2F5 and 4E10 that may target the membrane-proximal region of gp41 ectodomain [26-28]. The third variable region (V3) of gp120 is a "principal neutralizing determinant (PND)." Although major V3-specific antibodies are isolate-specific and neutralize only T-cell line adapted viruses or limit primary isolates, recently studies have also shown that some V3-specific monoclonal antibodies are able to neutralize primary isolates across clades [2, 29]. It becomes clear that these broadly neutralizing antibodies are unusual in that they are recognize either discontinuous epitopes or special conformational epitopes.

The hypervariable region (the V3 domain) of the envelope glycoprotein gp120 is highly immunogenic and was once considered "the principal neutralizing determinant (PND)." However, the V3 domain has been a controversial target for HIV-1 vaccine design mainly because of the highly variable nature of the sequence [1, 2, 85]. As a result, most V3-specific antibodies from the sera of early-infected patients or immunized animals are isolate-specific and neutralize only T-cell line adapted viruses or a very narrow range of primary isolates. However, recent data demonstrated that broadly reactive anti-V3 antibodies did exist, and some V3-specific poly- and monoclonal antibodies were able to neutralize a range of HIV-1 primary isolates across clades [86-90]. In addition, the V3 domain is accessible on native virus envelope [91].

The oligosaccharide components of glycoproteins have been implicated to play important roles in modulating protein's folding, stability, immunogenicity, and various cellular activities [30-33]. HIV-1 has two envelope glycoproteins, gp120 and gp41. They form trimeric complexes of heterodimers on the viral surface. Both are significantly glycosylated. The outer envelope glycoprotein gp120 carries about 24 N-glycans and the carbohydrates constitute about half of the molecular weight of gp120 [34-36]. The transmembrane glycoprotein gp41 carries 4 conserved N-glycans and the carbohydrates make 20-30% of its molecular mass [37, 38]. There are three major types of N-glycans in N-linked glycoproteins, namely, the high-mannose type, the complex type, and the hybrid type [39]. In the case of HIV-1 gp120, the nature (type) of N-glycans on individual glycosylation sites for some HIV-1 strains have been elucidated [34-36]. An important observation is that, by alignment, corresponding N-glycosylation sites among different HIV-1 strains seem to carry the same type of N-glycans [34-36].

Many studies have implicated that glycosylation affects the local or global conformations of peptides and proteins [8, 53-55]. For example, glycosylation usually stabilizes local conformations and induce turn-like structures of a polypeptide chain [53, 55, 56]. Experiments have demonstrated that not only the size, but also the nature and linkage type of the attached sugar chain, would have an impact on the underneath polypeptide conformations [57-61]. According to the carbohydrate analysis, the V3 domain of gp120 carries three conserved N-glycans within or adjacent to the loop, one complex type at N301, and two high-mannose type N-glycans at the N295 and N332 positions (HXB2 numbering), respectively [34-36]. Therefore, it is conceivable to think that individual N-glycans within or adjacent to the V3 domain will certainly influence the domain's conformations. This will, in turn, affect the antigenicity and immunogenicity of the V3 domain, particularly when a conformational epitope is involved. However, gp120 itself is too heterogeneous to be used for elucidating the detailed effects of glycosylation on local conformations of the V3 domain, even if site-specific mutation can selectively remove individual N-glycans within or adjacent to the V3 loop. For example, a typical gp120 has about 24 N-glycans but each N-glycan may exist in several different isoforms. As a result, over 100 glycoforms for a recombinant gp120 would exist [31]. Such heterogeneity in structure makes it extremely difficult to decipher the structure-function relationship of a given glycoprotein, and may sometimes yield confusing information as in the case of the immunogenicity of gp120 glycosylation mutants [40, 49]. To have a clear understanding of the roles that carbohydrates play in a glycoprotein and, particularly, to explore HIV-1 glycopeptides as novel immunogens, homogeneous materials are required. Synthesis seems to be the only practical means to provide various homogeneous glycopeptides for subsequent structural and biological studies.

While glycopeptides containing monosaccharides or a small oligosaccharide moiety can be prepared by conventional solid-phase peptide synthesis using glyco-amino acid derivatives as building blocks [110-112], the construction of large, biologically relevant glycopeptides carrying native N-glycans is still a challenging task [110, 113, 114], mainly because oligosaccharide chains, if pre-attached during solid-phase peptide synthesis, are susceptible to the acidic conditions used for peptide deprotection and cleavage from the solid support. On the other hand, no general chemical method is available to attach a sugar chain to a pre-assembled free polypeptide in a site-specific manner to form a full-size natural glycopeptide. To solve the problem, the current inventors and others have been exploring a novel chemoenzymatic approach using an endo-β-N-acetylglucosaminidase (ENGase) for adding an oligosaccharide to a pre-assembled polypeptide [115, 116]. Endo-β-N-acetylglucosaminidases (ENGases) are inherently a class of hydrolytic enzymes, but some possess significant transglycosylation activity and are able to transfer a N-glycan to a N-acetylglucosamine (GlcNAc) moiety in a GlcNAc-peptide acceptor to form a new glycopeptide. Endo-A from *Arthrobacter* can transfer a high-mannose type N-glycan to a GlcNAc-containing peptide [117], while Endo-M isolated from *Mucor hiemalis* prefers complex type N-glycan in transglycosylation [60, 118, 119]. Therefore, the distinct substrate specificity of the two endoglycosidases in transglycosylation will allow the construction of different glycoforms of glycopeptides.

The chemoenzymatic approach consists of two key steps: solid-phase peptide synthesis to prepare a GlcNAc-containing peptide precursor and the Endo-A or Endo-M catalyzed transfer of the N-glycan to the acceptor to accomplish the synthesis of the target glycopeptides.

Although the chemoenzymatic method allows a quick assembling of large glycopeptides, it still suffers with some weakness, such as the relatively low transglycosylation yield (generally 10-20%), the product hydrolysis, and the limitations of using only natural N-glycans as the donor substrates. Thus, it would be advantageous to develop a synthesis method to create synthetic homogeneous glycopeptides with increased transglycosylation without the limitation of using only natural N-glycans, wherein the synthetic homogenous glycopeptides may be used for conformational studies and for use as immunogens that induce broadly neutralizing antibodies.

SUMMARY OF THE INVENTION

In one aspect, the present invention relates to synthetic V3 glycopeptides and scaffold-based trivalent V3 glycopeptides for use as immunogens synthesized by applying a novel chemoenzymatic approach.

In another aspect, the present invention relates to a method of generating a synthetic glycopeptide, the method comprising;

- preparing a polypeptide by solid-phase peptide synthesis to prepare a GlcNAc-containing peptide precursor; and
- enzymatically adding an oligosaccharide to the synthesized peptide, wherein the oligosaccharide is a synthetic oligosaccharide oxazoline, and applicable enzymes include Endo-A or Endo-M.

Specifically, the chemical synthesis of the oligosaccharide oxazolines corresponding to the core of N-glycans is summarized in Scheme 1, shown below. The synthesis of the Man β1,4GlcN disaccharide core was achieved through stereo-controlled β-glycosylation of intermediates 1 and 2, followed by selective inversion of the Glc C-2 configuration to give 4. Compound 4 was changed to 6 via protecting group manipulations and was glycosidated with the mannosyl imidate to give the tetrasaccharide 7, which was then converted to the fully acetylated derivative 8. Finally, treatment of 8 with TMS-Br/$BF_3$ $Et_2O$ for oxazoline formation [128], followed by de-O-acetylation gave the desired tetrasaccharide oxazoline 9. The disaccharide oxazoline 11 was synthesized from 4 by similar protecting group manipulations and oxazoline formation (Scheme 1).

Scheme 1. Chemical synthesis of the di- and tetra-saccharide oxazolines

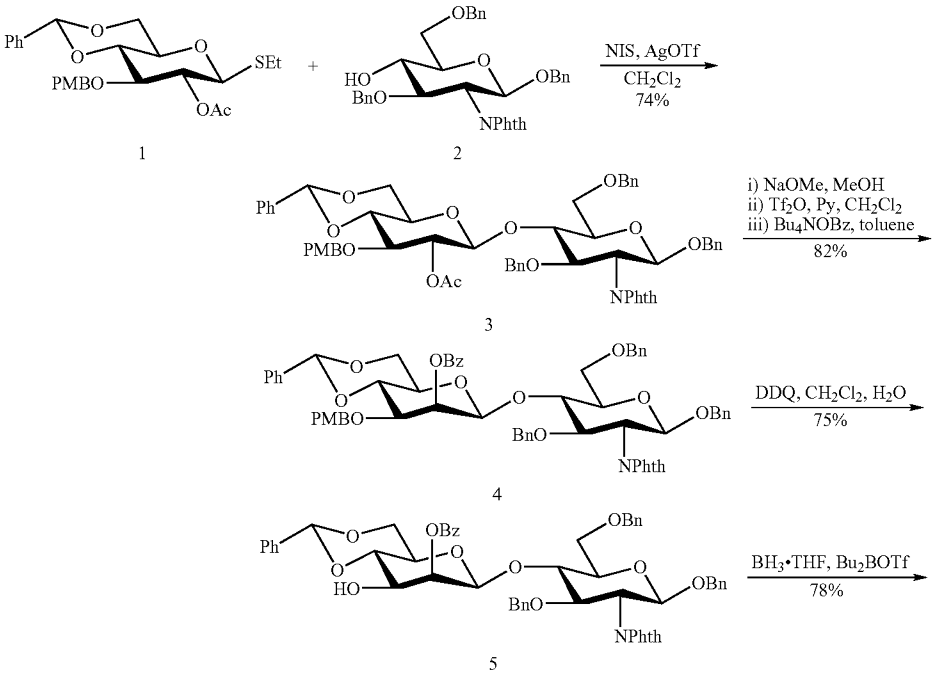

1 2 3 4 5

-continued
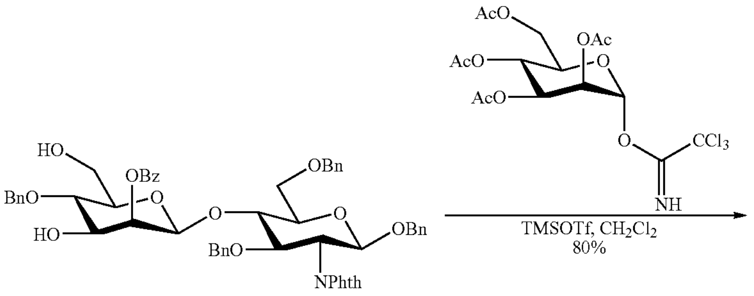
6
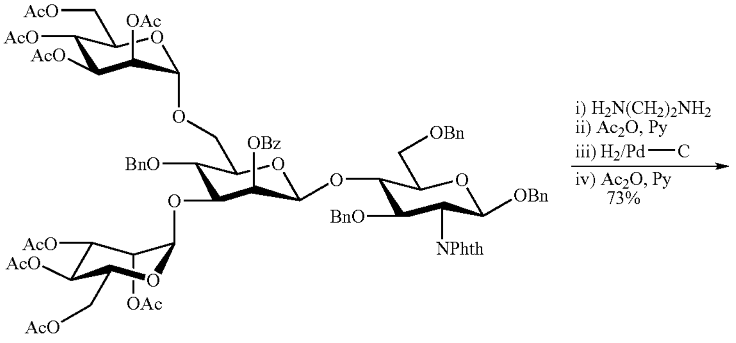
7
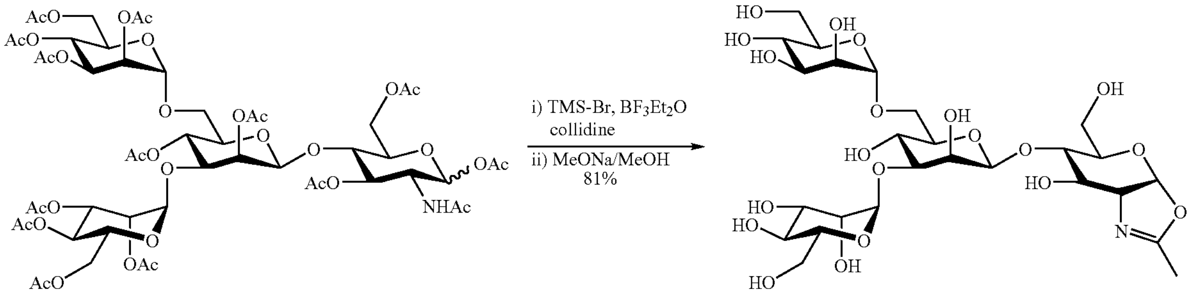
8 9
4
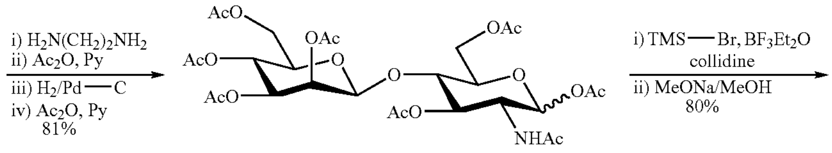
10
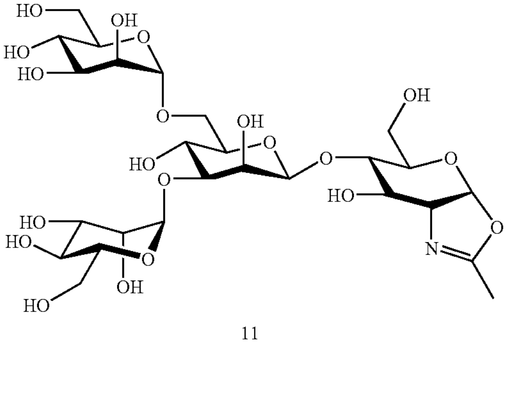
11

The synthetic oligosaccharide oxazolines were used as donor substrates for constructing N-glycopeptides, wherein a GlcNAc-peptide served as the glycosyl acceptors and Endo A or Endo-M were effective in catalyzing the reaction to form a glycopeptides, as shown in Scheme 2 below.

In yet another aspect, the present invention relates to determining a method of generating an immune response, the method comprising:

administering to a mammal a V3 domain glycopeptide carrying one or two core pentasaccharide N-glycans, Scheme 2. ENG ase-catalyzed synthesis of a gp 120 fragment carrying the core trisaccharide

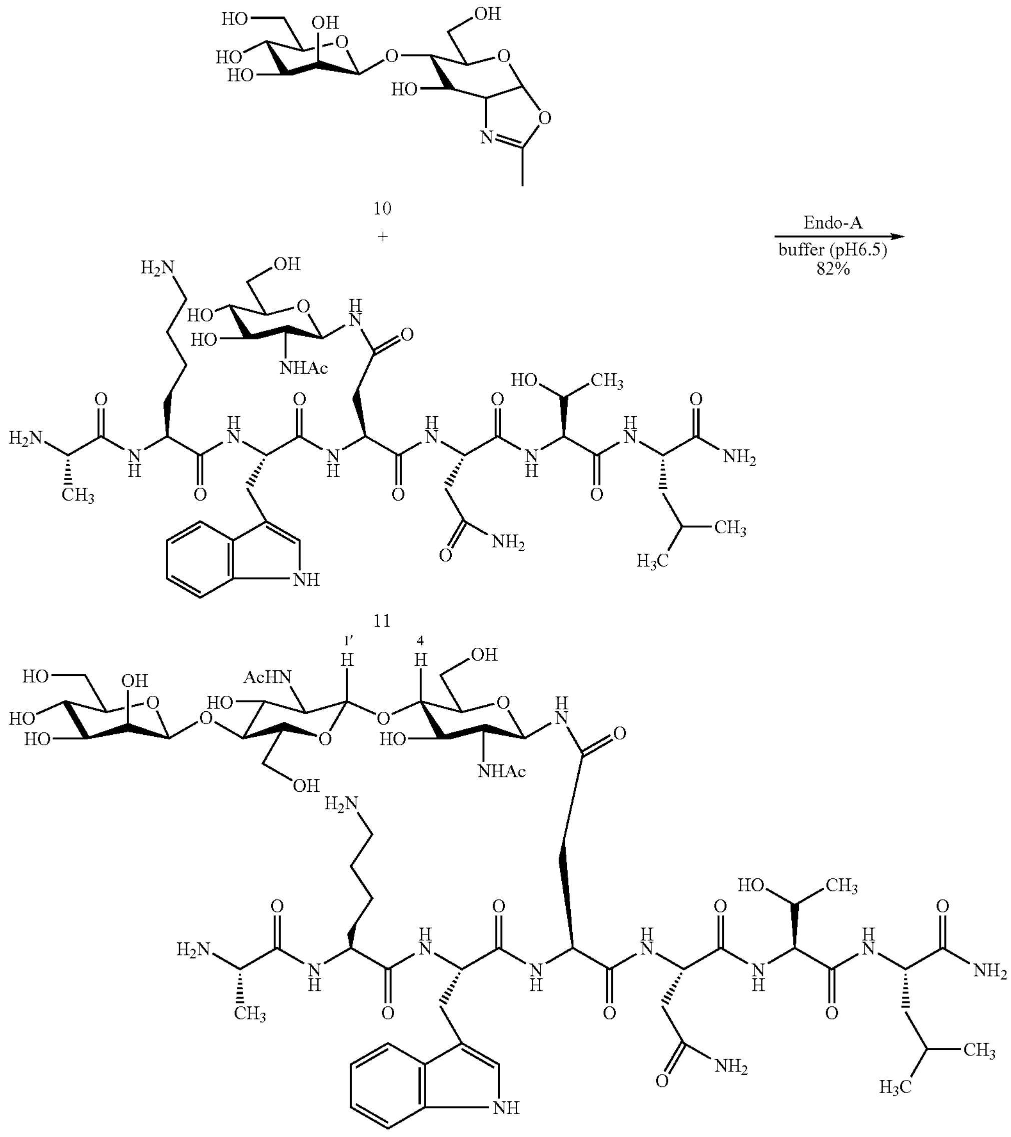

10

11

12

In another aspect, the present invention relates to synthesis of V3 glycoproteins, the method comprising:

synthesizing a peptide containing at least one N-acetylglucosamine (GlcNAc) moiety to form GlcNAc-peptide acceptor; wherein the N-acetylglucosamine (GlcNAc) moiety is positioned at N301, or positioned at N295 and N332;

transglycosylating a tetrasaccharide oxazoline and the GlcNAc-peptide acceptor under the catalysis of the enzyme Endo-A to form V3 domain glycopeptides carrying one or two core pentasaccharide N-glycans, HB-V3-G2M3 and HB-V3-(G2M3)2.

HB-V3-G2M3 and HB-V3-(G2M3)2 as described above in an amount to induce production of antibodies there against.

In yet another aspect, the present invention relates to antibodies, including polyclonal and monoclonal, and production thereof, wherein the antibody is immunoreactive with a V3 domain glycopeptide of the present invention.

In still a further aspect, the present invention contemplates a process for producing an antibody, which is immunoreactive with a V3 domain glycopeptide of the present invention comprising the steps of:

(a) introducing the V3 domain glycopeptide into a live animal subject; and (b) recovering antisera comprising antibodies specific for the V3 domain glycopeptides.

Other features and advantages of the invention will be apparent from the following detailed description, and claims.

DETAILED DESCRIPTION OF THE INVENTION

Spectroscopic (CD and NMR) studies have demonstrated that linear V3 peptides exist in solutions largely as random, unordered structures, although cyclization of full-size V3 peptides induces some conserved secondary structures such as a β-turn at the tip (GPGR or GPGQ) of the loop [62-74]. X-ray structural studies of synthetic V3 peptides complexed with various V3-specific monoclonal antibodies have demonstrated that neutralizing mAbs recognized distinct but highly similar conformations of the V3 epitopes [75-78]. The data suggested that the V3 domain of gp120 might adopt some common conformations shared by primary isolates. A more recent study demonstrated that the broadly neutralizing antibodies targeting V3 domain were all somewhat conformation-sensitive, while most type-specific anti-V3 antibodies are more specific for the linear sequence [29]. The data suggest that V3 conformations are important for raising more broadly neutralizing antibodies. However, the effects of the conserved N-glycans on the V3 conformations have not been appropriately addressed, probably due to the difficulties in obtaining homogeneous, full-size V3 glycopeptides. Only a few limited studies attempted to address the issue using a model system. For example, Laczko et al. attached mono- or di-saccharide moieties at the sites near the tip of a short V3 peptide and found that the addition of the sugar moiety near the tip stabilized the type II β-turn conformation of the V3 peptide [79]. In another study, Huang et al introduced two monosaccharide residues at potential O-glycosylation sites of a 24-mer linear V3 peptide and also found that the sugar moieties enhanced the population of the β-turn conformation at the tip [80, 81]. Moreover, it was found that the model V3 glycopeptide actually showed enhanced binding to a V3-specific neutralizing antibody 5α in comparison with the non-glycosylated V3 peptide [81]. Unfortunately, the effects of the full-size conserved N-glycans on the V3 domain conformations are unclear, and the solved three-dimensional structures of the gp120 core [3, 82-84], in which the V3 loop together with the N-glycans was deleted, provided little information about the V3 domain structure.

Figure 1:
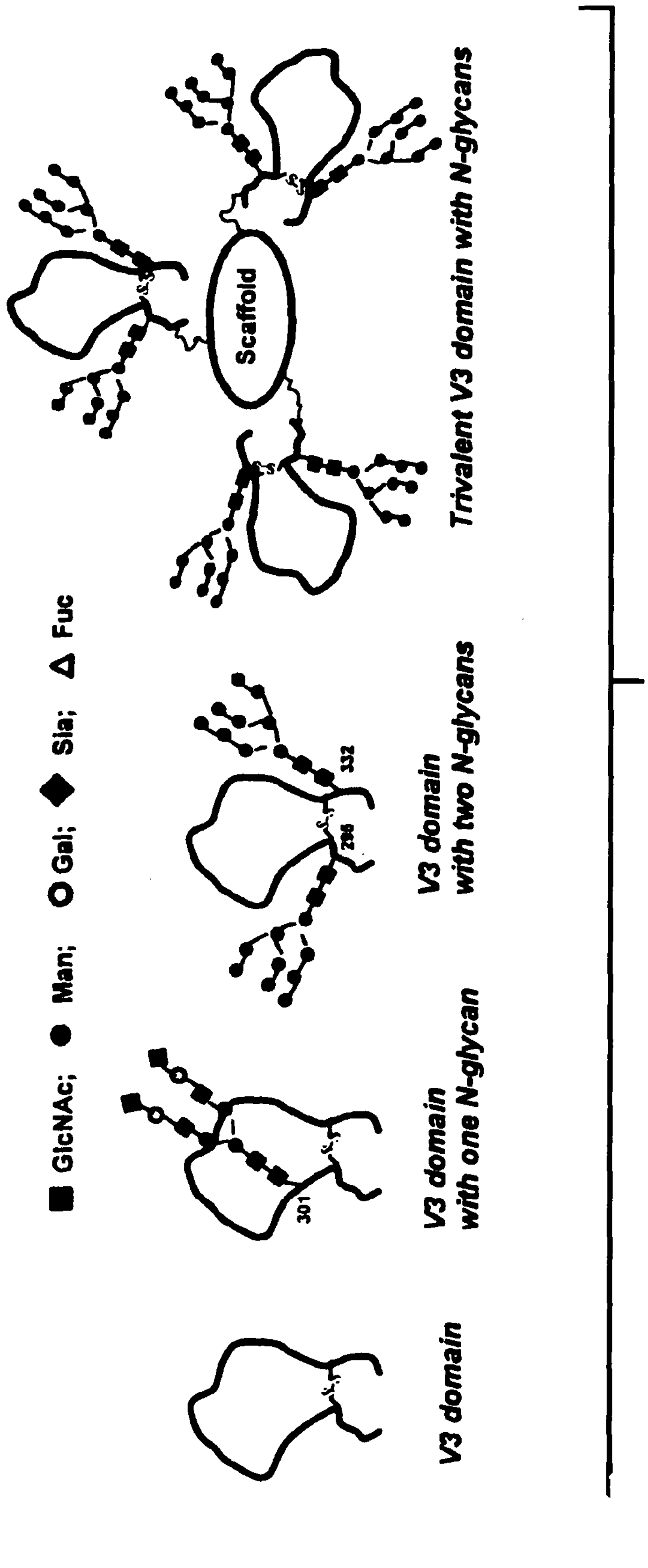
FIG. 1 shows typical synthetic immunogens of the present invention.

Despite the variation of the linear sequence flanking the crown of the V3 loop, the V3 domain from various HIV-1 isolates does share some notable conserved elements, including a fixed size (30-35 amino acids), a highly conserved tip sequence (GPGR or GPGQ), a conserved β-turn structure at its tip, and a disulfide bond at its base (Cys296-Cys331, HXB2 numbering) [3, 94]. Notably, the three N-glycans within or adjacent to the V3 loop are also highly conserved among distinct HIV-1 strains. The N-glycan at N301 of the V3 loop is conserved among most viral isolates except for that of subtype D. The N-glycan at N332 of the C-terminal side of V3 loop is conserved among viral isolates from most subtypes, except for subtype E, while the N-glycan at the amino-terminal side of V3 loop is highly conserved among subtype B isolates [4-6, 41, 42, 95]. The functional importance of the V3 domain in HIV-1 pathogenesis also suggests that the V3 domain constitutes an important target for vaccine development. For example, despite the variability, the V3 domain determines the HIV tropism (R5 vs. X4 viruses) [96], and plays a critical role in chemokine coreceptor binding during HIV-1 infection [97-99]. General structures of the V3-glycopeptides as described herein are shown in FIG. 1. The V3 glycopeptide moiety contains a complex type N-glycan at N301, or two high-mannose type N-glycans at the N295 and N332 positions, respectively (HXB2 numbering).

It should be noted that many "naked" (non-glycosylated) V3-loop peptides were tested as immunogens in the past [2, 71, 90, 102-106], but very few could raise broadly neutralizing antibodies. This is understandable, given that the majority of humoral responses would be directed to the (more immunogenic) variable regions, which would result in isolate-specific antibodies. Conformational epitope of the V3 peptide immunogens is another issue that has to be taken into account. Thus, the present inventors theorize that the N-glycans in the V3-glycopeptide immunogen mask, at least partially, the undesired epitopes at the variable regions and redirect the immune response to the more conserved epitopes on the V3 domain. Thus, the glycopeptides with high-mannose N-glycans (FIG. 1) are particularly interesting because the N-glycans at N295 and N332 (HXB2 numbering) are part of the epitope of the broadly neutralizing antibody 2G12 [4-6].

Overall, the novel HIV-1 glycopeptides of the present invention, which combine the viral peptide and oligosaccharide moieties as an integrated unity, are conceptually different from the sole peptide or carbohydrate immunogens. It should be noted that gp120 itself, either wild-type or engineered, might be difficult to become a successful HIV-1 vaccine, because the whole glycoprotein is too heterogeneous and contains too many (unwanted) B-cell epitopes that "dilute" the immune response to the neutralizing epitopes. However, in contrast, the homogeneous HIV-1 glycopeptides of the present invention are homogeneous with well defined structure, and they are immunologically focused on the epitopes.

Figure 2:
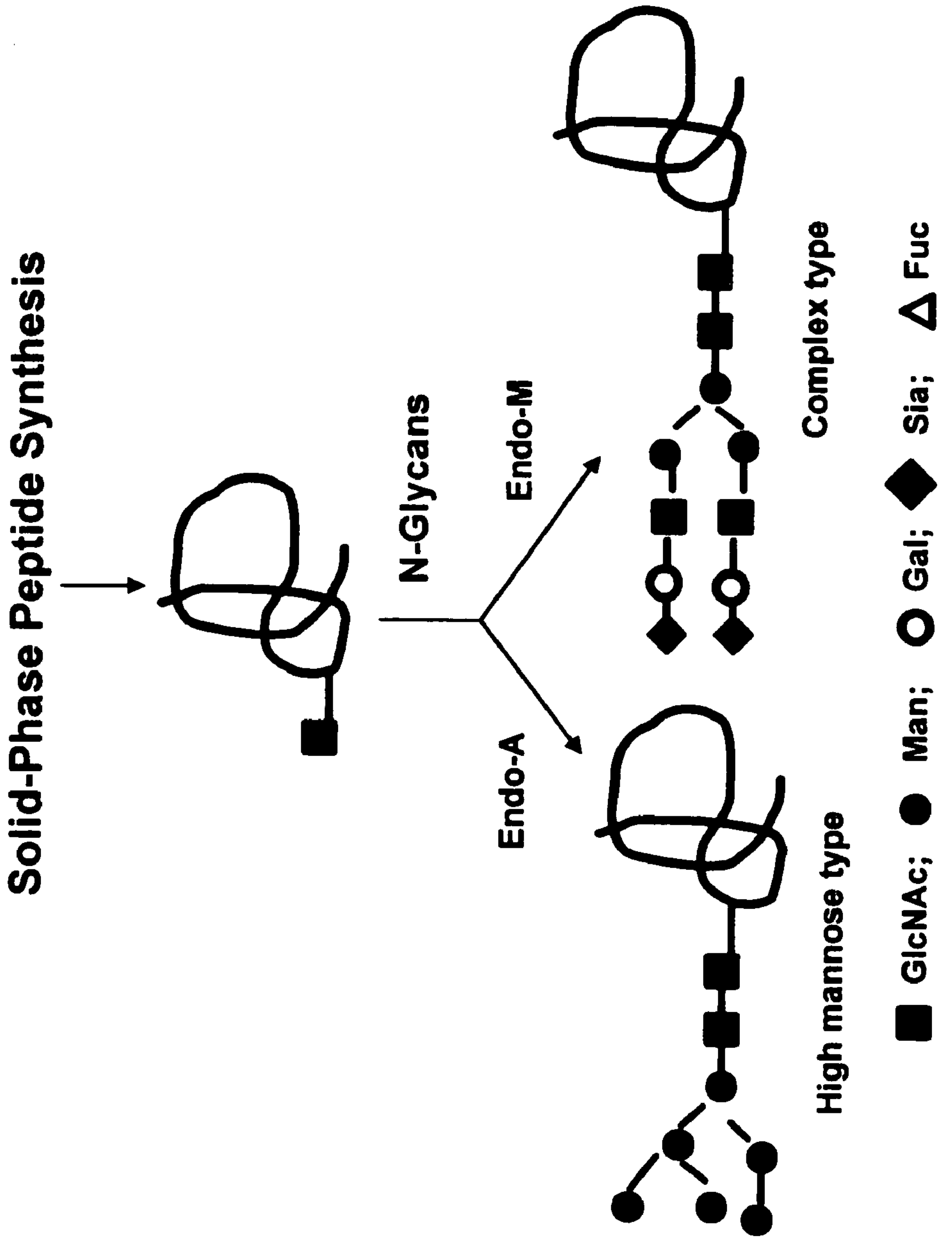
FIG. 2 shows chemoenzymatic synthesis of N-glycopeptides.

No general chemical method was available heretofore to attach a sugar chain to a pre-assembled free polypeptide in a site-specific manner to form a full-size natural glycopeptide. To solve the problem, a novel chemoenzymatic approach using an endo-β-N-acetylglucosaminidase (ENGase) for adding an oligosaccharide to a pre-assembled polypeptide [115, 116]. Endo-β-N-acetylglucosaminidases (ENGases) are inherently a class of hydrolytic enzymes, but some possess significant transglycosylation activity and are able to transfer a N-glycan to a N-acetylglucosamine (GlcNAc) moiety in a GlcNAc-peptide acceptor to form a new glycopeptide. Endo-A from *Arthrobacter* can transfer a high-mannose type N-glycan to a GlcNAc-containing peptide [117], while Endo-M isolated from *Mucor hiemalis* prefers complex type N-glycan in transglycosylation [60, 118, 119]. Therefore, the distinct substrate specificity of the two endoglycosidases in transglycosylation will allow the construction of different glycoforms of glycopeptides, as shown in the chemoenzymatic synthesis of N-glycoeptides in FIG. 2.

Figure 3:
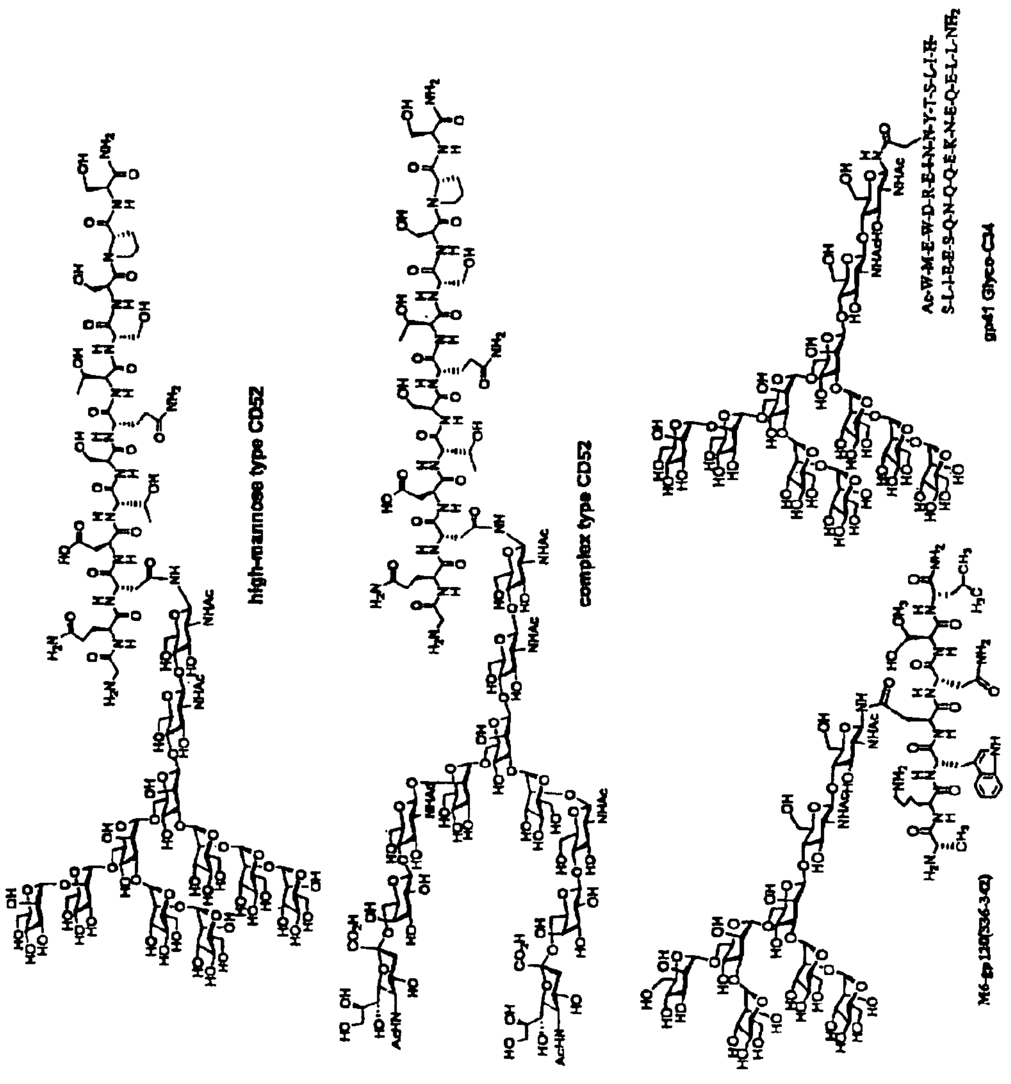
FIG. 3 shows additional representative glycopeptides synthesized by the chemoenzymatic methods of the present invention

The chemoenzymatic approach consists of two key steps: solid-phase peptide synthesis to prepare a GlcNAc-containing peptide precursor and the Endo-A or Endo-M catalyzed transfer of the N-glycan to the acceptor to accomplish the synthesis of the target glycopeptides. Using the chemoenzymatic approach, we have successfully synthesized a series of biologically interesting glycopeptides, including the native CD52 glycoprotein antigens [124], and some HIV-1 gp120 and gp41 glycopeptides [116, 123, 125]. FIG. 3 shows some representative glycopeptides synthesized by the chemoenzymatic approach.

The present inventors found that the use of synthetic oligosaccharide oxazolines, the putative transition-state analogs, has led enhancement of the transglycosylation yield (75-85%). The results suggest that the oligosaccharide oxazolines as transition-state analogs are kinetically more favorable substrates for an efficient N-glycopeptide synthesis than the natural N-glycans.

The improved method not only broadened the substrate availability, but also led to a very high-yield synthesis of large N-glycopeptides. The improved method is briefly described here. First, the chemical synthesis of the di- and tetra-saccharide oxazolines corresponding to the core of N-glycans was summarized in Scheme 1, as shown hereinabove.

Endo-A catalyzed transglycosylation of the di- and tetra-saccharide oxazolines was also tested with the larger gp41 peptide acceptor, GlcNAc-C34.[125]. It was found that the oligosaccharides could also be effectively transferred to the large GlcNAc-C34 by Endo-A to form the glycopeptides 14 and 15 in 73 and 75% yields, respectively (Scheme 3).

Scheme 3. ENGase-catalyzed synthesis of a large gp41 glycopeptide carrying the core tri- and penta-saccharide

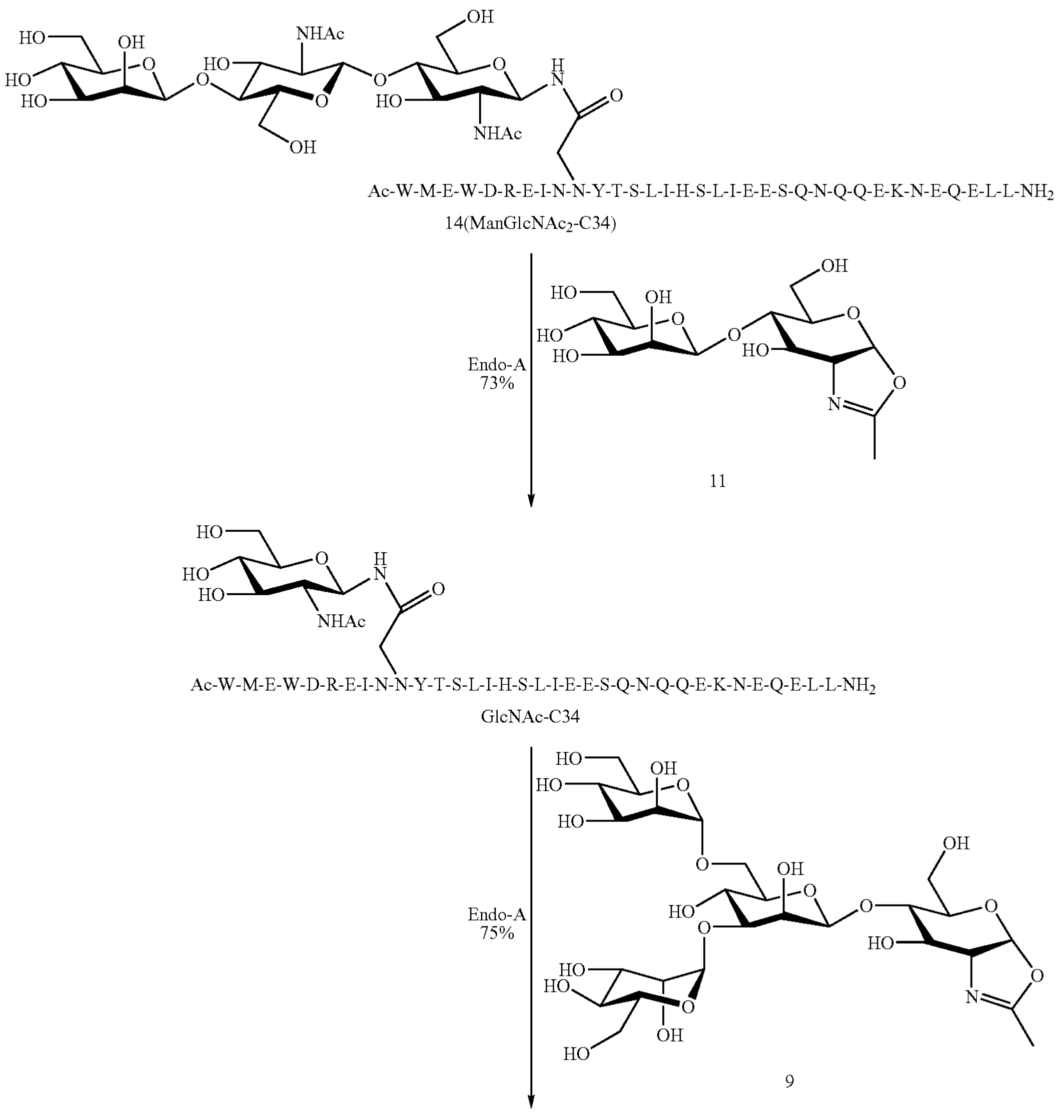

Ac-W-M-E-W-D-R-E-I-N-N-Y-T-S-L-I-H-S-L-I-E-E-S-Q-N-Q-Q-E-K-N-E-Q-E-L-L-$NH_2$

14(ManGlcNAc$_2$-C34)

11

Ac-W-M-E-W-D-R-E-I-N-N-Y-T-S-L-I-H-S-L-I-E-E-S-Q-N-Q-Q-E-K-N-E-Q-E-L-L-$NH_2$

GlcNAc-C34

9

-continued

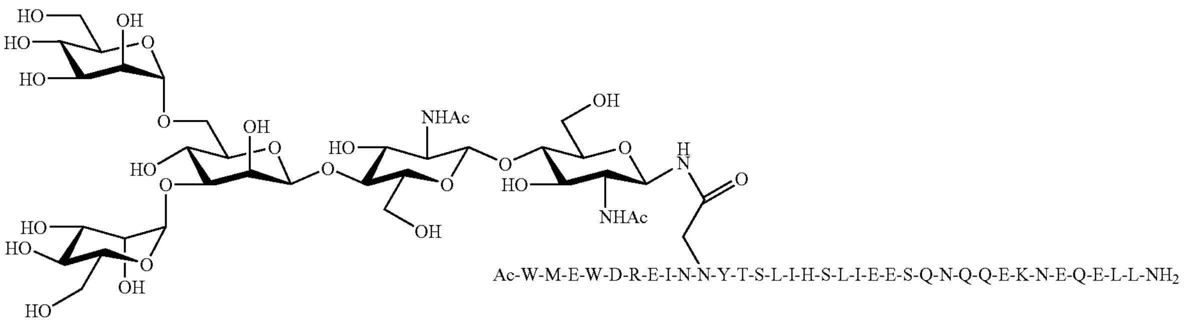

15($Man_3GlcNAc_2$-C34)

The glycopeptides were again characterized by ESI-MS and NMR analysis. Further structural characterization of glycopeptide 15 was performed by pronase digestion that yielded a single Asn-linked oligosaccharide, which was identical to the authentic Asn-linked core pentasaccharide $Man_3GlcNAc_2Asn$ by $^1H$-NMR, ESI-MS, and Dionex HPAEC analysis.

It was also observed that while the Manβ1,4GlcNAc-oxazoline and $Man_3GlcNAc$-oxazoline acted as an efficient substrate for transglycosylation, the resulting glycopeptide $ManGlcNAc_2$-C34 (14) was resistant to Endo-A hydrolysis, and the glycopeptide $Man_3GlcNAc_2$-C34 (15) was hydrolyzed only slowly by Endo-A (data not shown).

This suggests that the oligosaccharide oxazolines as transition-state analogs are much more active substrates than the ground state N-glycopeptides, thus being kinetically favorable for product accumulation.

It should be mentioned that Danishefsky et al recently reported a total chemical synthesis of two gp120 20-mer glycopeptides containing either a high-mannose type or a hybrid type N-glycan. The synthesis took over 50 steps and encountered numerous practical problems including deprotections and final ligations [130, 131].

In comparison, the chemoenzymatic method of the present invention provides a very efficient and quick access to various homogeneous HIV-1 glycopeptides.

Further, the synthesis methods of the present invention provide for the successful synthesis of the designed HIV-1 V3 glycopeptide immunogens.

Structures shown in FIG. 1 were constructed herein. The V3 domain of gp120 carries three conserved N-glycans within or adjacent to the loop, one complex type at N301, and two high-mannose type N-glycans at the N295 and N332 positions (HXB2 numbering), respectively [34-36]. Moreover, the high-mannose N-glycans at N295 and N332 is theorized to be part of the epitope for antibody 2G12 [4, 5, 25].

For the synthesis of a target, such as HXB2 $gp120^{290}$-336, a peptide containing a N-acetylglucosamine (GlcNAc) moiety at N301, and a peptide containing two GlcNAc moieties at N295 and N332 positions, were first synthesized, which would be used as the precursor for the chemo-enzymatic synthesis.

The preparation of the 47-mer precursor GlcNAc-peptide (HB-V3-G) is depicted in Scheme 4 below.

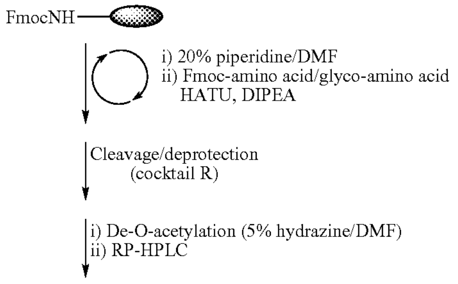

-continued

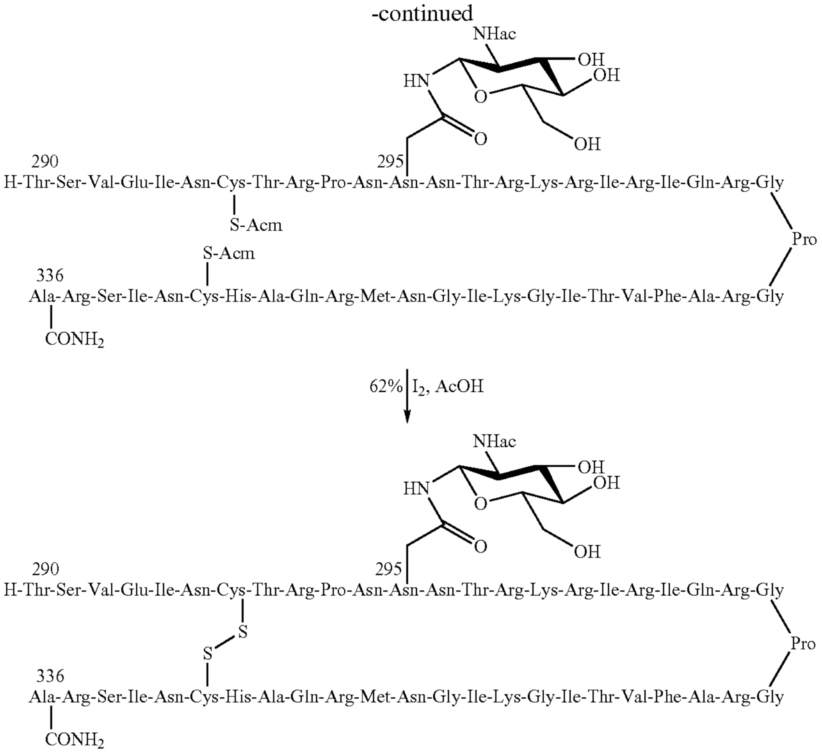

HB-V3-G

Briefly, Fmoc-($Ac_3$GlcNAc)Asn-OH was used as building block to replace the Asn residue at N301 in the automatic solid-phase peptide synthesis on a PAL-PEG-PS resin. The two Cys residues were temporarily protected as the Acm derivatives. The peptide was then retrieved from the resin with simultaneous side-chain deprotection by treatment with cocktail R (90:5:3:2, TFA-thioanisole-EDT-anisole). After de-O-acetylation with 5% aqueous hydrazine, the crude peptide was purified by RP-HPLC to give HB-V3-G-Acm with the two Cys residues being protected by Acm groups. Finally, the Acm protecting groups were removed by treatment with iodine, with simultaneous cyclization, to give the cyclic V3 peptide HB-V3-G. The peptide was isolated by reverse-phase HPLC and characterized by ESI-MS. Transglycosylation reaction between the tetrasaccharide oxazoline and the GlcNAc-peptide acceptor under the catalysis of the enzyme Endo-A (phosphate buffer, pH 6.5) was monitored by RP-HPLC. It was found that the enzymatic reaction proceeded smoothly to give a sole new product that was eluted slightly earlier than the starting material HB-V3-G under the HPLC condition (Scheme 5).

Scheme 5. Synthesis of the cyclic V3 glycopeptide carrying a core pentasaccharide at N301

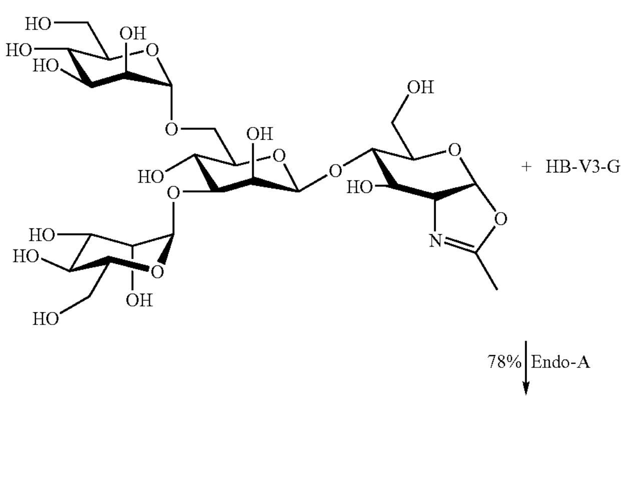

-continued

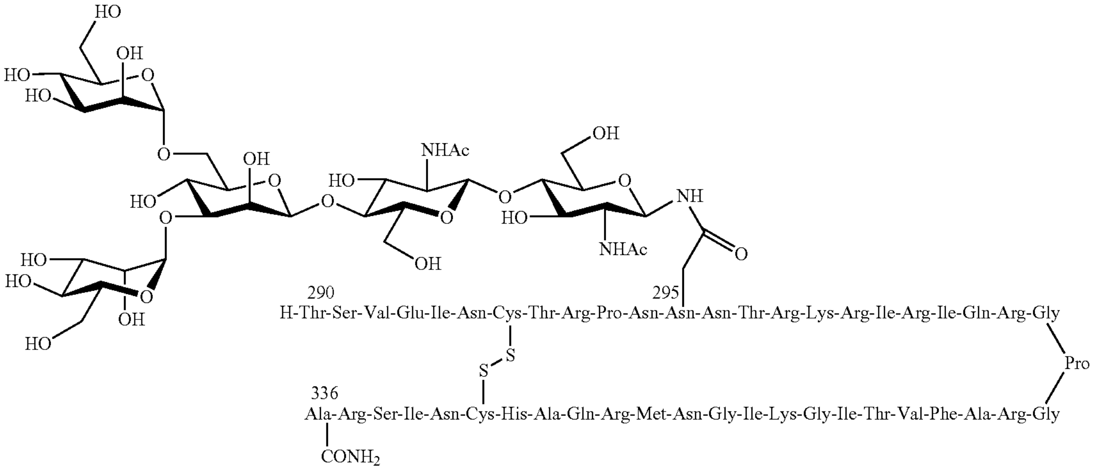

HB-V3-G2M3

The product was easily purified by preparative HPLC (yield: 78%) and was characterized by ESI-MS (calculated M=6196.50; found: M=6197.20±0.87 after deconvolution of the MS data). Further structural characterization of glycopeptide V3-G2M3 was performed by pronase digestion that yielded a single Asn-linked oligosaccharide identical to the authentic Asn-linked core pentasaccharide $Man_3GlcNAc_2Asn$ by $^1H$-NMR, ESI-MS, and Dionex HPAEC analysis. The results indicated that the transferred oligosaccharide was specifically attached to the GlcNAc moiety of the precursor GlcNAc-peptide.

Notably, heretofore, no synthesis of a full-size, cyclic V3 peptide carrying a core pentasaccharide N-glycan was ever synthesized. Next, synthesis of a full-size V3 domain carrying two N-glycans at the N295 and N332 positions, respectively was prepared. First, the preparation of the precursor peptide HB-V3-G2 was similarly performed as for the synthesis of HB-V3-G by solid-phase peptide synthesis (Scheme 6).

Scheme 6. Solid-phase synthesis of the cyclic V3 peptide carrying two GlcNAc moieties

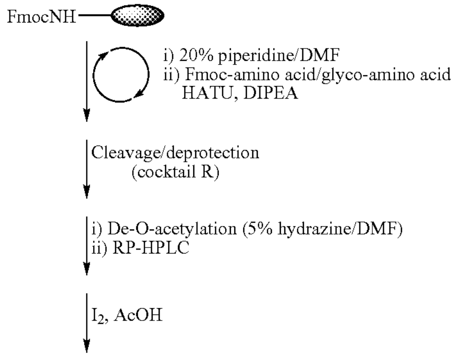

-continued

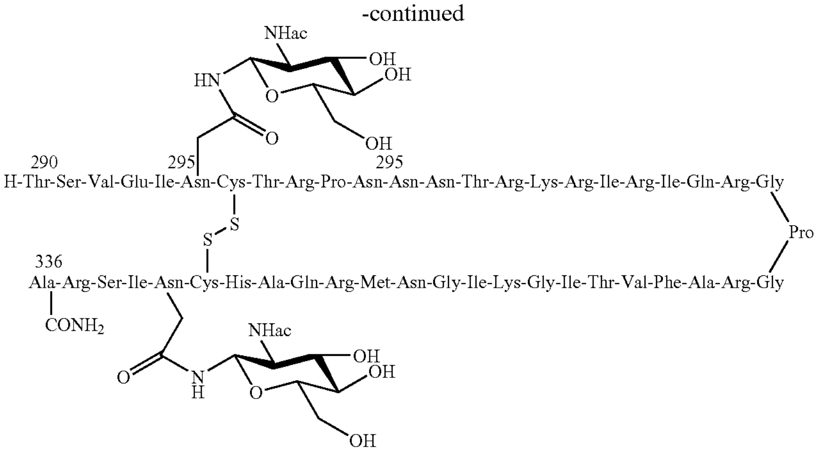

HB-V3-G2

The transglycosylation using the tetrasaccharide oxazoline as the donor substrate was performed in the same way as described above. When an excess of the oxazoline donor substrate (3 molecular equivalent per GlcNAc moiety in the acceptor) was used, it was observed that Endo-A catalyzed transfer proceeded very efficiently to give the desired product HB-V3-(G2M3)2 carrying two core pentasaccharide N-glycans (Scheme 7).

Scheme 7. Synthesis of the cyclic V3 glycopeptide carrying two core pentasaccharide moieties

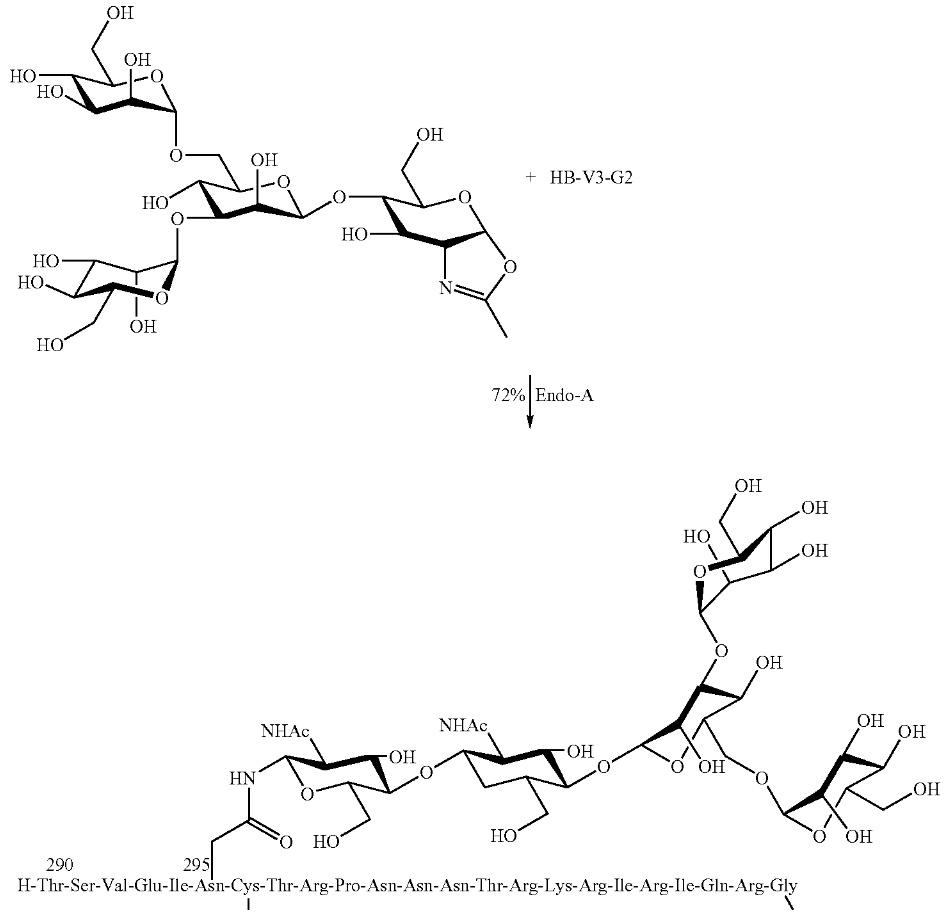

-continued

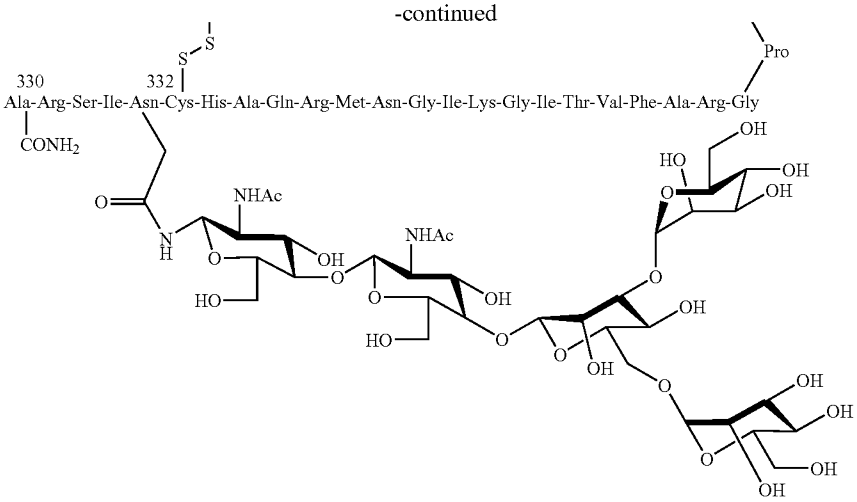

HB-V3-(G2M3)2

Figure 4:
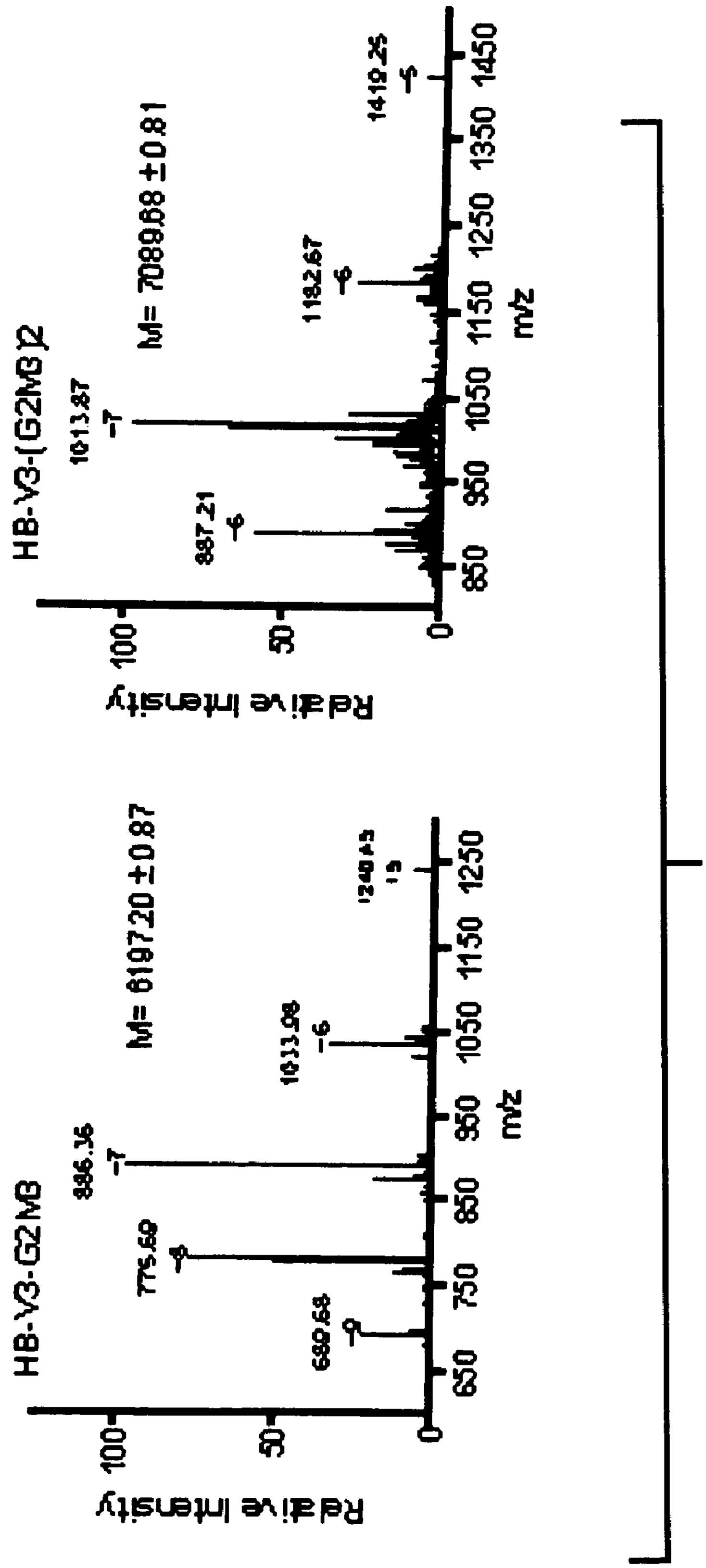
FIG. 4 shows ESI-MS spectra of the synthetic V3 glycopeptides.

The isolated yield was 72%. Unexpectedly, the highly efficient synthesis was a surprise, because it was theorized that it would be difficult to add two N-glycans simultaneously to the likely sterically-hindered two GlcNAc residues in the cyclic V3 peptide. This is the first example to simultaneously transfer two N-glycans to a peptide for constructing a very large glycopeptide by the chemoenzymatic approach. Again, the glycopeptide was carefully characterized by ESI-MS and selective transformation analysis. The ESI-MS spectra of the synthetic V3 domain glycopeptides carrying one or two core pentasaccharide N-glycans, HB-V3-G2M3 and HB-V3-(G2M3)2, respectively, are shown in FIG. 4.

With the successful synthesis of the V3 glycopeptides carrying the core pentasaccharide N-glycan(s), some preliminary studies were performed on their conformations and compared their conformations with the non-glycosylated V3 domain (HB-V3). Two spectroscopic methods for conformational studies, namely, the circular dichroism spectroscopy (CD) and Fourier transformation infrared spectroscopy (FTIR) were used for the initial studies. The CD spectra were recorded on a Jasco spectropolarimeter (Model J-810, Jasco Inc., Japan) at 23° C. in a phosphate buffer (5 mM, pH 7.0) and the concentrations of the samples were 20-40 μM.

Figure 5:
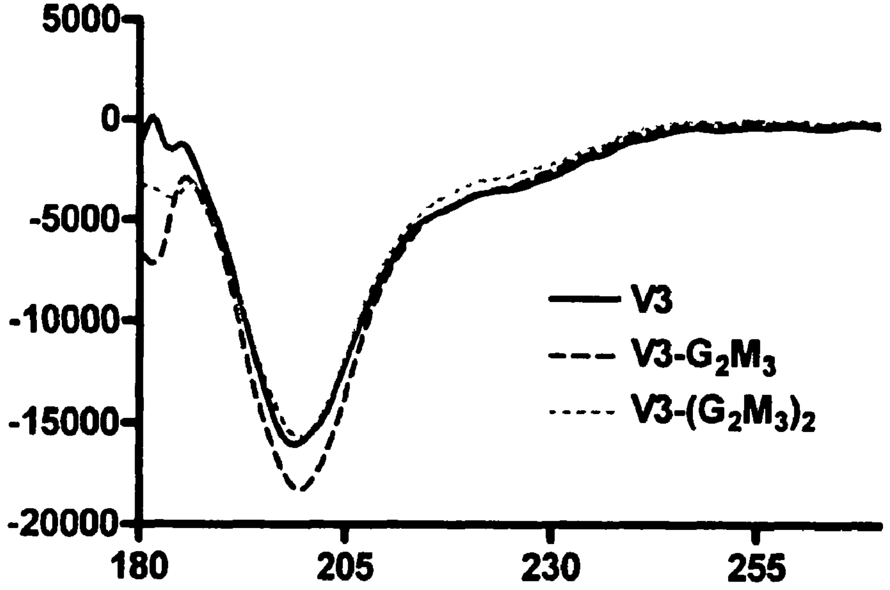
FIG. 5 shows the CD spectra of the V3 peptide and glycopeptides in phosphate.

As shown in FIG. 5, showing the CD spectra of the V3 peptide and glycopeptides in phosphate buffer, the CD spectra showed a strong negative band at 198 nm, indicating that the V3 peptide and glycopeptides took largely an unordered structure in aqueous solution. Calculation of the possible secondary structures using the K2d software revealed that the glycopeptide HB-V3-(G2M3)2 carrying two N-glycans (at N295 and N332) showed an enhanced β-turn or loop structure (39%) over the glycopeptide HB-V3-G2M3 carrying one N-glycan (at N301) (27%) or the non-glycosylated peptide HB-V3 (24% β-turn or loop structure). Although the calculation is only a rough estimate, the results implicated the influence of N-glycans on the V3 conformations.

The conformations were investigated by ATR-FTIR (attenuated total reflectance-fourier transformation infrared spectroscopy). The advantage of infrared protein analysis is its ease to use for studying proteins in aqueous media at any buffer conditions [132, 133]. From the infrared spectrum, the secondary structure content such as β-turns or loops may be determined more accurately than CD analysis. Moreover, the high specificity of the amide-I band allows detection of conformational changes in protein and peptides with high sensitivity.

Figure 6:
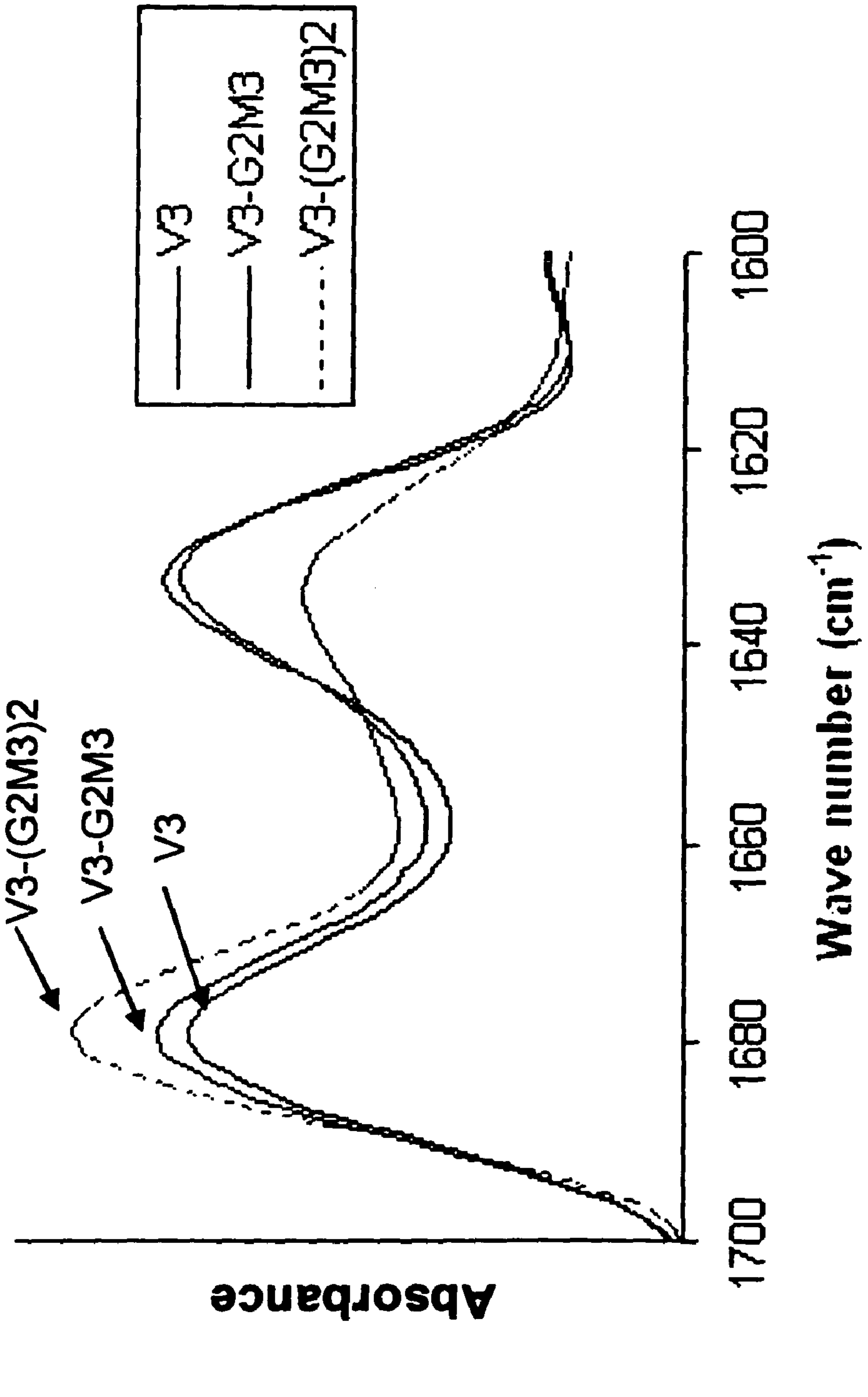
FIG. 6 shows the FT-IR spectra of the V3 peptide and glycopeptides.

The FT-IR spectra were measured with a Bruker Tensor 27 FTIR instrument (Bruker Optics, Bullerica, Mass.) equipped with an MCT detector cooled with liquid nitrogen. As shown in FIG. 6, showing the FT-IR spectra of the V3 peptide and glycopeptides, a clear difference in the FT-IR spectra was observed for the glycosylated and non-glycosylated V3 peptides. The glycopeptides clearly showed an enhanced band at 1682 $cm^{-1}$ (an indication of β-turn or loop structures) and a decreased band at 1633 $cm^{-1}$ (an indication of random or unordered structure) over the non-glycosylated V3 peptide. The results suggest that glycosylation indeed affects the global conformations of the V3 domain. The glycopeptide HB-V3-(G2M3)2, which carries two N-glycans at N295 and N332, respectively, demonstrated the highest β-turn secondary structure. It should be pointed out that the possibility was ruled out that the added N-glycans themselves would contribute to the observed difference in the IR spectra because a control with a high-concentration of the N-glycans alone was run and there was no apparent observance at 1982 and 1633 $cm^{-1}$.

It is generally expected that glycosylation of peptides and proteins may make them more stable against heat denaturation, freezing/thawing, and protease digestion [31]. To test this, a quick experiment was performed on the resistance of the synthetic V3 glycopeptides against different proteases. The protease furin was reported to be able to cleave the V3 domain of gp120 at the sequence 302-312 [134-136]. Therefore, the stability of the synthetic glycopeptides toward furin digestion was initially examined. The enzyme was obtained from Sigma and the digestion was monitored by HPLC and ESI-MS analysis.

Figure 7:
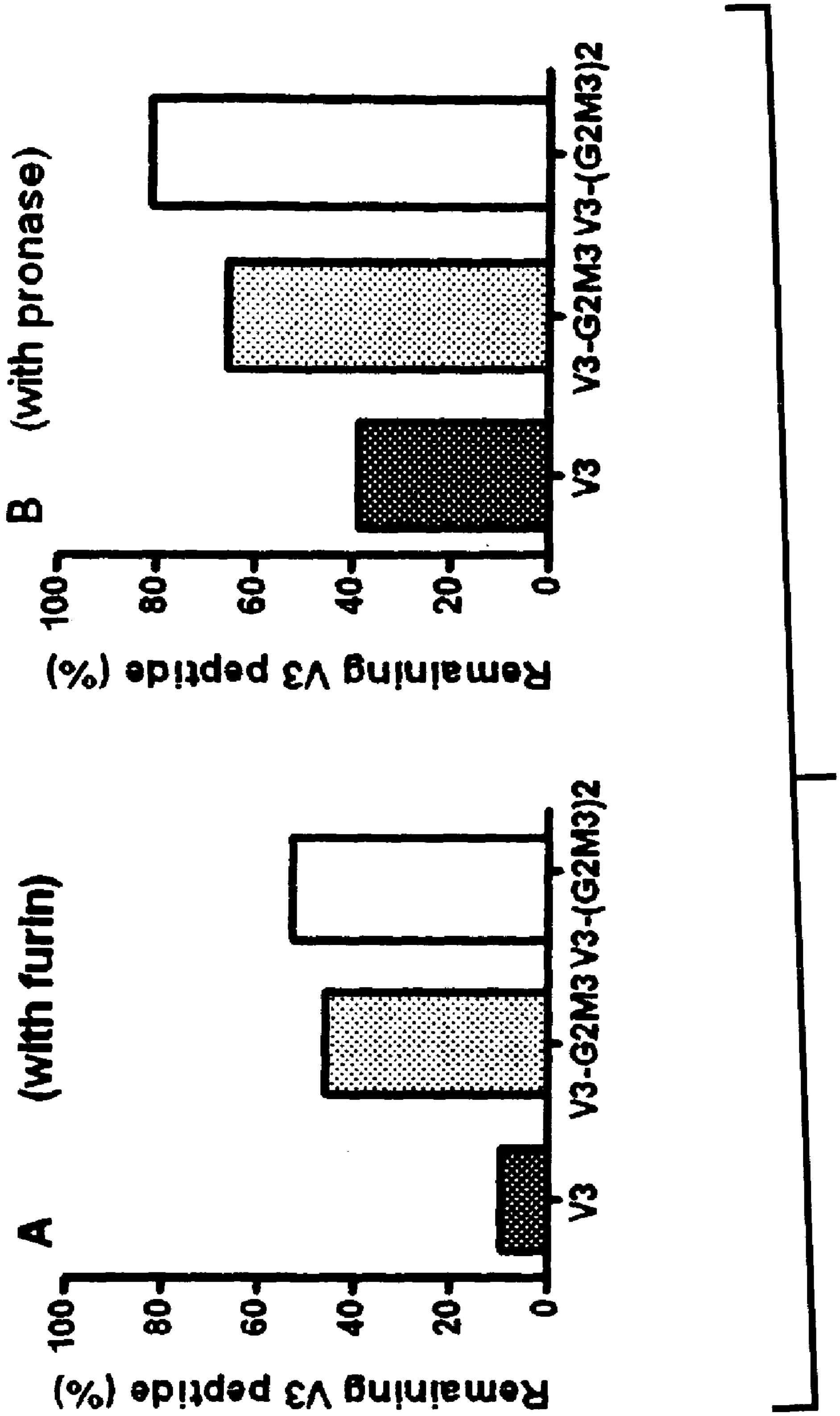
FIG. 7 shows the stability of the glycosylated and non-glycosylated V3 peptides toward protease digestion.

FIG. 7 shows the stability of the glycosylated and non-glycosylated V3 peptides toward protease digestion. FIG. 7A is a graph for digestion with furin, under reaction conditions involving a solution of each peptide (40 μM) in a phosphate buffer (pH 7.0, total 30 μl) incubated with 10 units of furin (Sigma; a unit being defined by the amount of furin that hydrolyzes one pmol substrate in 1 minute under the optimal condition) for 16 hours at 30° C., and the remaining starting peptide was quantified by HPLC and confirmed by ESI-MS determination. FIG. 7B is a graph for digestion with pronase under reaction conditions involving a solution of each peptide (40 μM) in a phosphate buffer (pH 7.4, total 100 μl) incubated with 125 ng of pronase (Sigma) for 40 minutes at 30° C., and the remaining starting peptide was quantified by HPLC and confirmed by ESI-MS determination.

It was found that furin could hydrolyze the V3 peptide and glycopeptides, but the V3 glycopeptides was much more stable than the non-glycosylated V3 peptide (FIG. 7A). The results suggest that the N-glycan(s) can offer protection against furin digestion. Next, the stability of the V3 glycopeptides against pronase digestion was tested. The pronase (Actinase E, Sigma) is a mixture of at least three proteolytic activities. As demonstrated in FIG. 7B, again, the glycopeptides are more resistant against pronase digestion than the "naked" V3 peptide. The glycopeptide HB-V3-(G2M3)2 that bears two core pentasaccharides was most stable toward protease digestion among the three under the conditions described in FIG. 7. These experimental data implicate that the cyclic V3 glycopeptides are likely to be more stable in vivo than the non-glycosylated V3 peptides when used as immunogens.

There are three N-glycans within or adjacent to the V3 loop that are highly conserved among distinct HIV-1 strains. The N-glycan at N301 (HXB2 numbering) of the V3 loop is a complex type N-glycan and is conserved among most viral isolates except for that of subtype D. The N-glycans at N295 and N332 are high-mannose type N-glycans that are highly conserved among subtype B isolates [4-6, 41, 42, 95].

Biochemical analysis (carbohydrate composition, SDS-PAGE, etc) of gp120 and its various site-specific glycosylation mutants indicated that the sites were actually occupied by N-glycans among all the HIV-1 strains analyzed [4-6, 34-36, 137]. Therefore, the HIV-1 V3-glycopeptides represent epitopes actually existing on native HIV-1 surface.

To prepare homogeneous V3-domain glycopeptides for structural and immunization studies, two typical types of the V3 domain glycopeptides derived from both X4 and R5 strains were chosen as targets. One is a 47-mer V3 glycopeptide corresponding to the sequence of $gp120^{291-336}$ from HIV-1 HXB2 strain (X4 tropic) that uses chemokine coreceptor CXCR4 for entry. The other one is a 46-mer V3 glycopeptide that is corresponding to the sequence of $gp120^{291-336}$ from the HIV-1 BAL strain (R5 tropic) that uses coreceptor CCR5 for entry. A complex type N-glycan is installed at the N301 position, and two high-mannose type N-glycans are attached at the N295 and N332 glycosylation sites (HXB2 numbering), respectively.

Cyclic glycopeptides were prepared for all the structural and immunization studies. It is to be noted that the two N-glycans at N295 and N332 (HXB2 numbering) comprise part of the epitope of the broadly neutralizing antibody 2G 12 [4-6].

Figure 8:
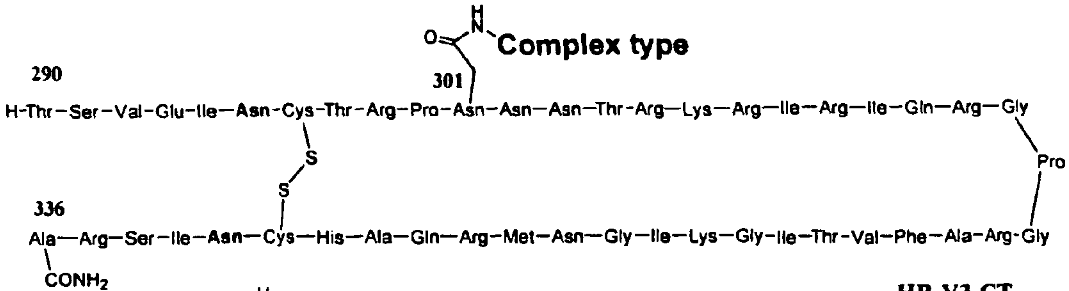
FIG. 8 shows the sequences and glycosylation types of the V3-domain of the HXB2 and BAL-strains.
Figure 8:
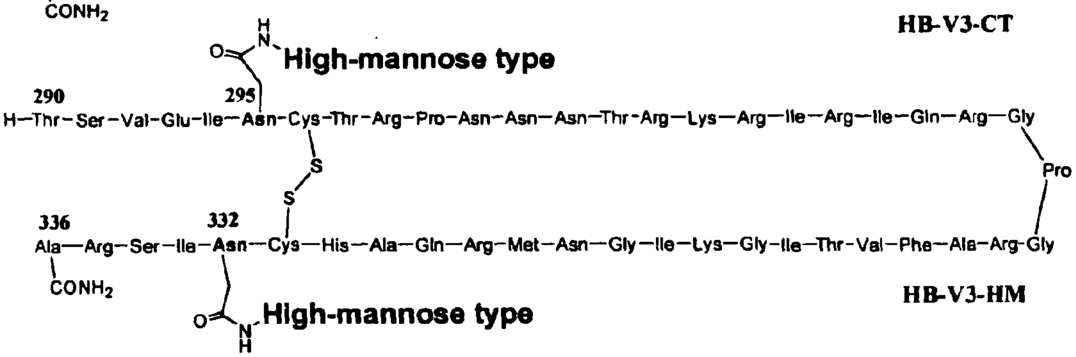
Figure 8:
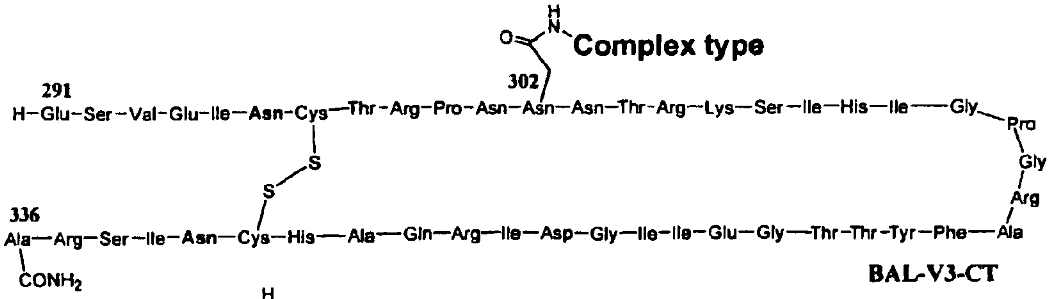
Figure 8:
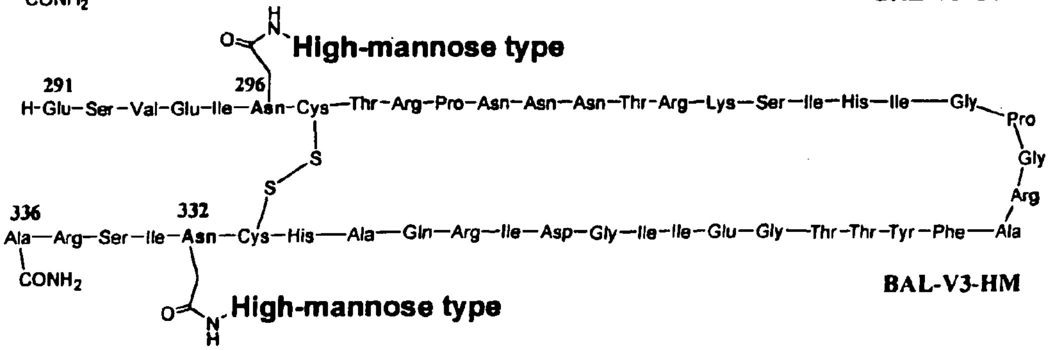

The amino acid sequences of the two types of V3 domain glycopeptide immunogens are shown in FIG. 8, including the sequence and glycosylation types of the V3-domain of HXB2 and BAL-strains.

The overall profiles of the two V3-domains are similar but the sequences flanking the tips are variable. The full lengths (47-mers) of the V3 domain sequences are chosen in order to include multiple T-helper epitopes and B-cell epitopes in the resulting glycopeptides (For T- and B-cell epitope mapping, please see: http://hiv-web.lanl.gov).

Therefore, the synthetic large V3 glycopeptides themselves are expected to be immunogenic enough to induce antibody responses in a formulation with an appropriate adjuvant.

Figure 9:
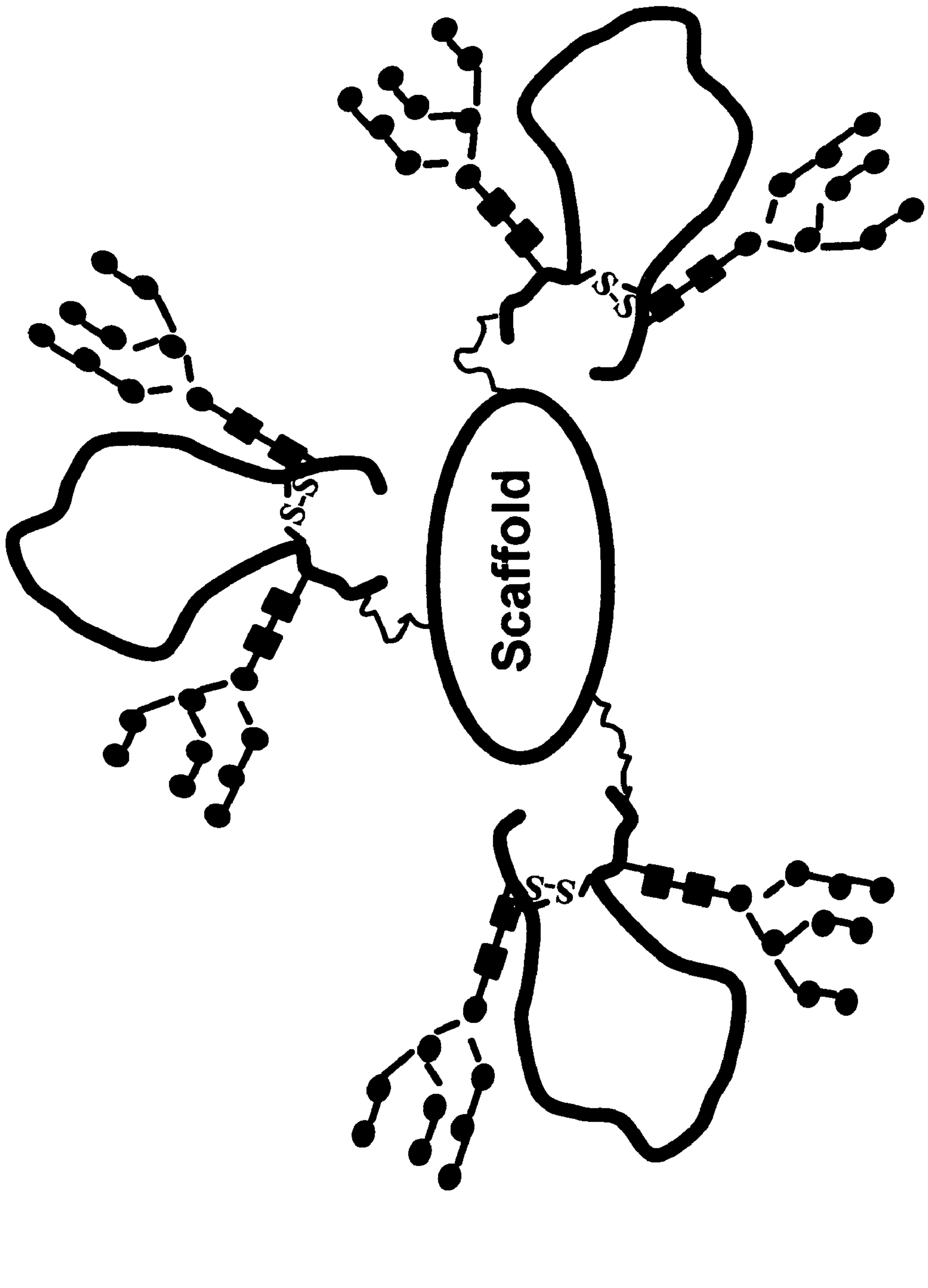
FIG. 9 shows a trivalent V3-domain glycopeptide that was synthesized by conjugating monomeric glycopeptide to a trivalent scaffold, to provide a synthetic trivalent conjugate as an immunogenic construct.

For comparative studies, a novel trivalent V3-domain glycopeptide was synthesized by conjugating the monomeric glycopeptide to a trivalent scaffold producing the construct shown in FIG. 9.

It is theorized that three strands of the V3-domain glycopeptide on a scaffold will make it more immunogenic. Moreover, the trivalent conjugates likely mimic the V3 domain presentation in the trimeric gp120 when the length of the spacer is appropriate.

The precursor GlcNAc-containing V3 peptide (HB-V3-G) was prepared that bears a GlcNAc moiety at N301 position and the GlcNAc-peptide precursor is ready for the synthesis of V3 glycopeptides containing a complete structure of the complex type N-glycan.

As shown in Scheme 8, a complex type N-glycan will be transferred to the N301 GlcNAc moiety by the Endo-M catalyzed transglycosylation.

Scheme 8. Synthesis of the complex type V3-glycopeptide HB-V3-CT

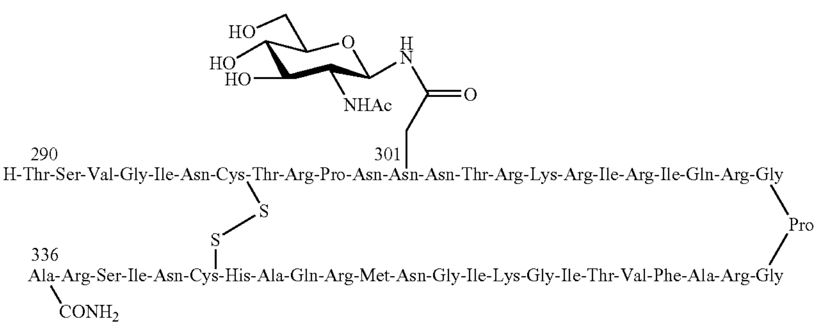

HB-V3-G

Enzyme: Endo-M Transglycosylation

Sialylglycopeptide or Oligosaccharide oxazoline

-continued
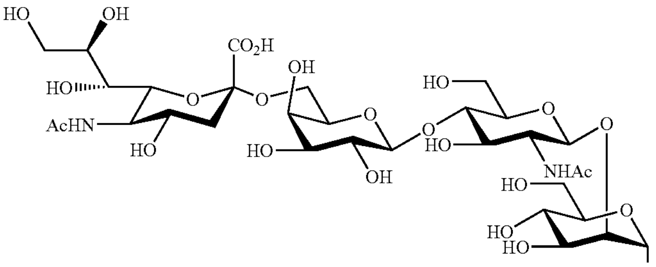
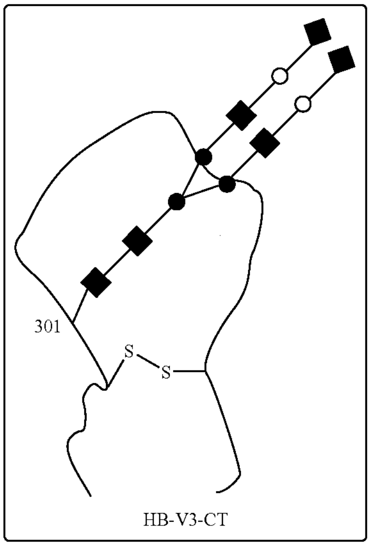
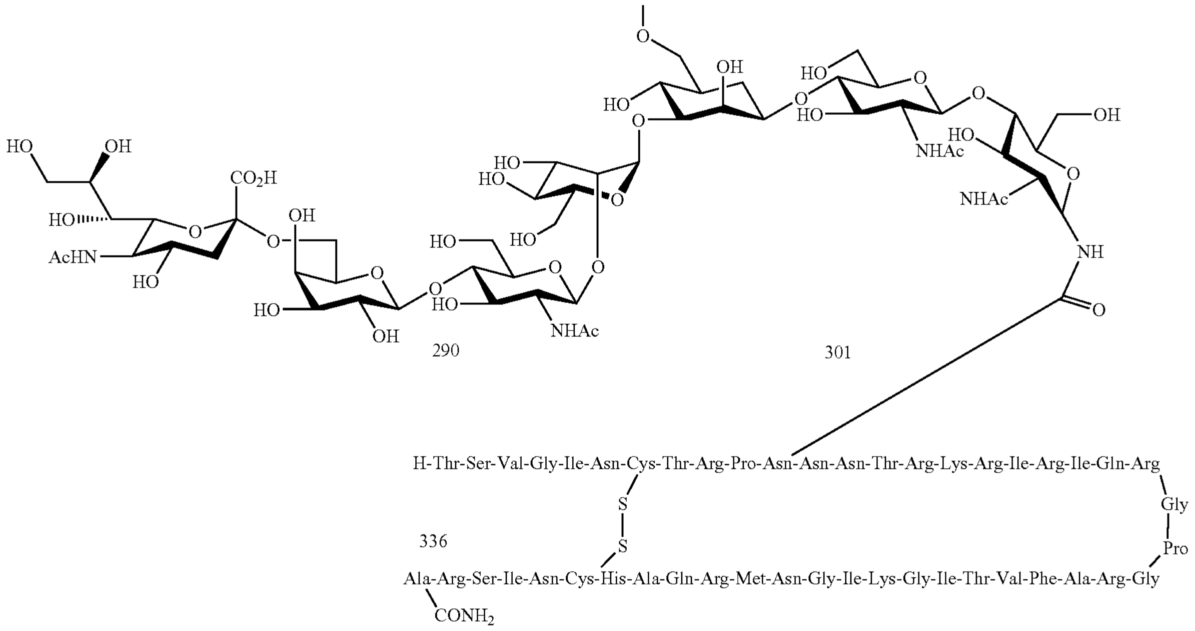
HB-V3-CT

As exemplified in the synthesis of complex type CD52 glycoprotein [124], the donor substrate will be a bi-antennary sialylglycopeptide (SGP), H-Lys-Val-Ala-Asn[(NeuAc-Gal-GlcNAc-Man)$_2$-Man-GlcNAc$_2$]-Lys-Thr-OH. The oxazoline derivative of the complex type N-glycan from the natural N-glycan as the donor substrate for more efficient transglycosylation was prepared according to Scheme 9.

Scheme 9. Synthesis of the complex type oligosaccharide oxazolines from natural N-glycans

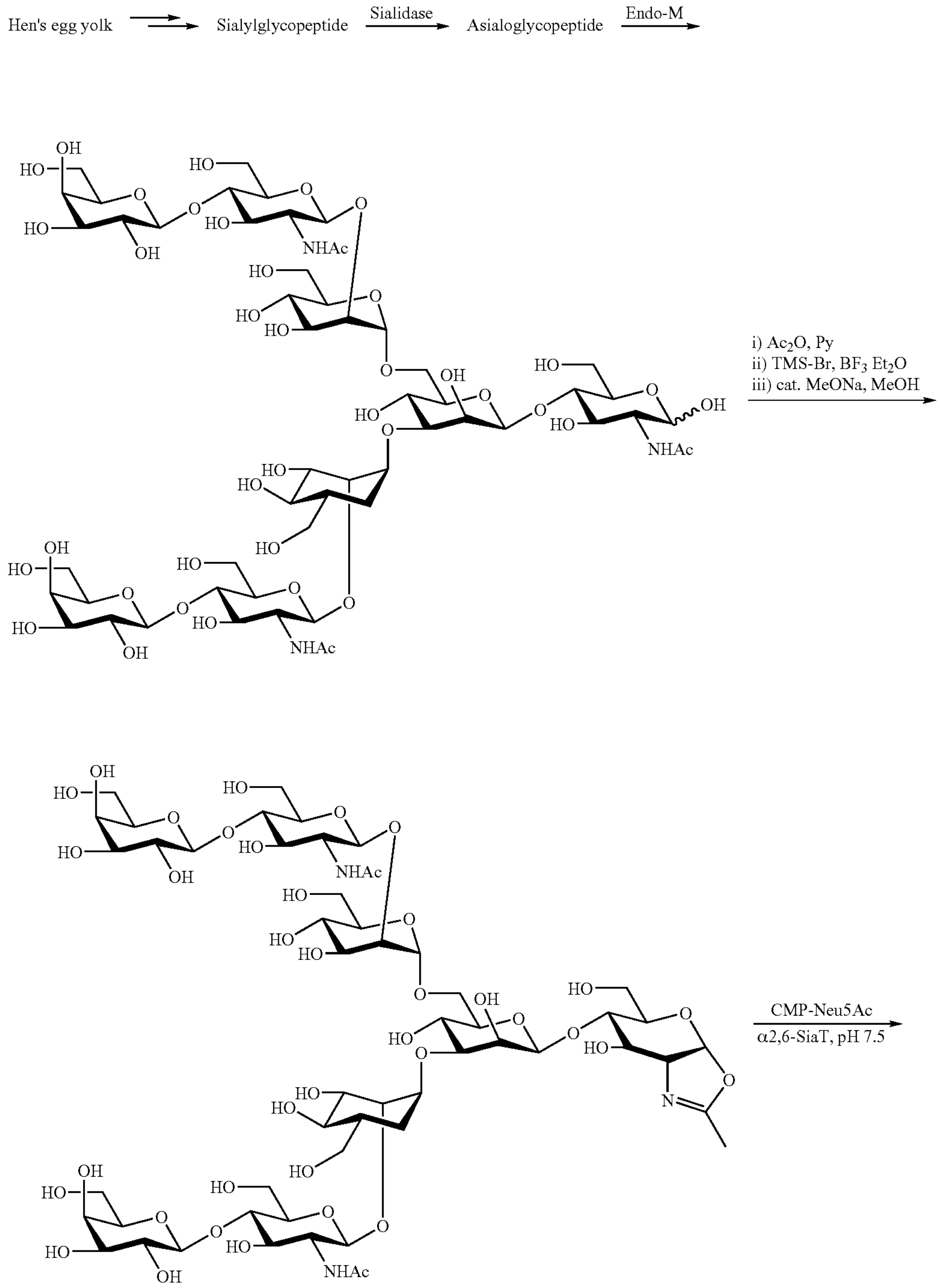

-continued

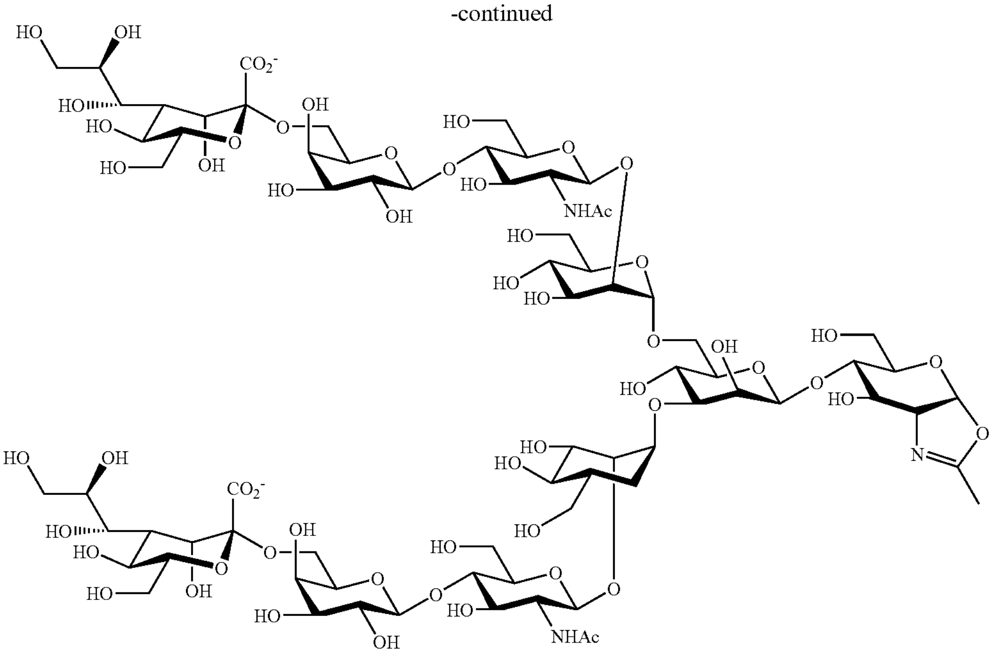

To perform detailed structure-function relationship such as glycoform-antibody affinity relationship studies, various homogeneous glycoforms are prepared from the parent glycopeptide. These will include: 1) removal of the sialic acid residues by sialidase treatment to give the neutral glycopeptide (HB-V3-CT1); and 2) further trimming of the sugar chain (removing the Gal residues) with a β-galactosidase to provide another glycopeptide HB-V3-CT2 (Scheme 10).

Scheme 10. Synthesis of the HB-V3-CT glycoforms of complex type

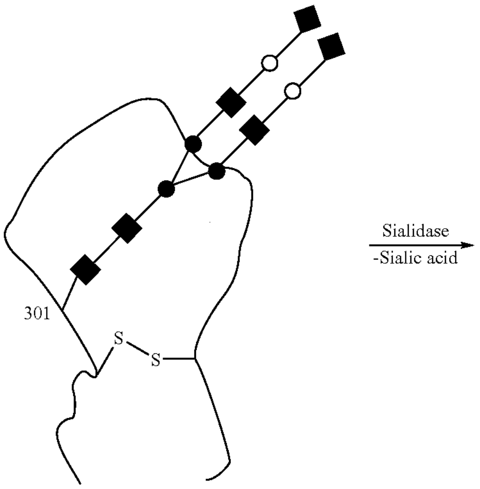

HB-V3-CT

-continued

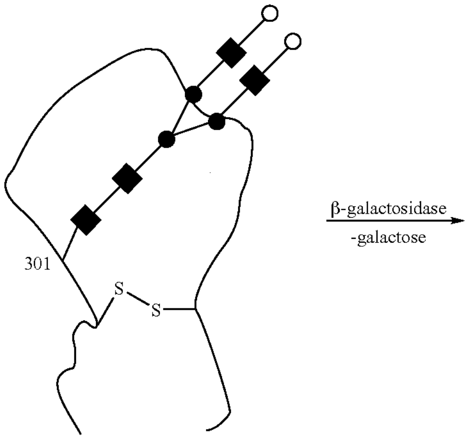

HB-V3-CT1

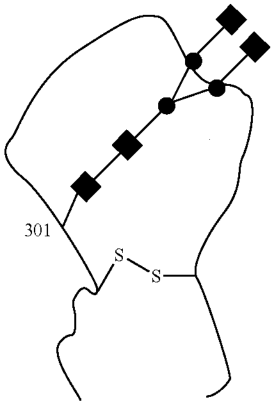

HB-V3-CT2

◆ GlcNAc; ● Man; ○ Gal; ◆ Sia; △ Fuc

All these glycoforms are present in HIV-1 gp120 as shown in the carbohydrate analysis of gp120 [34-36, 137].

V3-glycopeptides from both HXB2 strain (X4) and BAL strain (R5) that carry two high-mannose type N-glycans are synthesized.

To attach the largest high-mannose type N-glycan at the two N295 and N332 sites, the Endo-A catalyzed transglycosylation was performed using either the Man9GlcNAc2Asn directly or the corresponding Man9-oxazoline as the donor substrates.

The oxazoline derivative is prepared in several steps (Scheme 11).

Scheme 11. Synthesis of Man9 oxazoline from natural Man-glycan

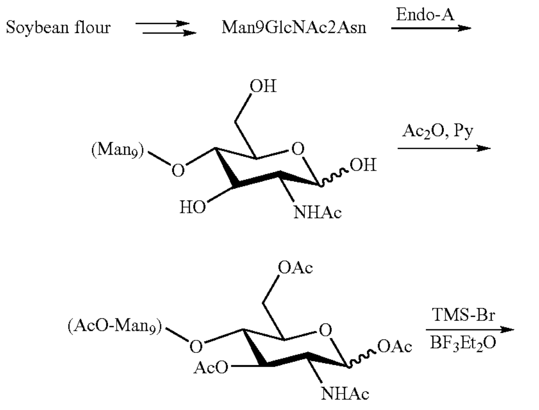

-continued

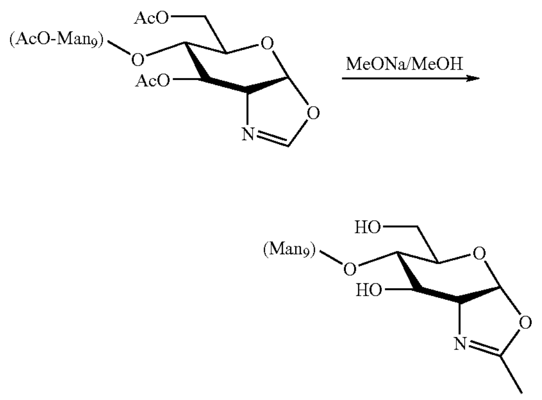

In addition to the Man9-glycopeptides, two additional glycoforms of the high-mannose type glycopeptides are prepared using Man6GlcNAc2Asn and Man5GlcNAc2Asn as the oligosaccharide donors, respectively, which are prepared from chicken ovalbumin.

This provides the truncated glycoforms of the high-mannose type glycopeptides, HB-V3-(G2M6)2 and HB-V3-(G2M5)2 (Scheme 12).

Scheme 12. Synthesis of HB-V3 glycoforms of high-mannose type

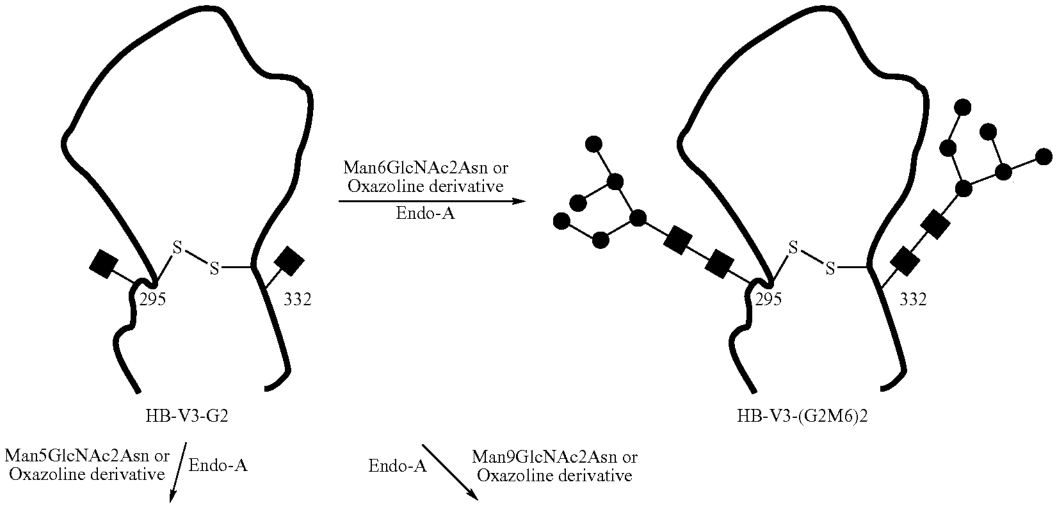

-continued

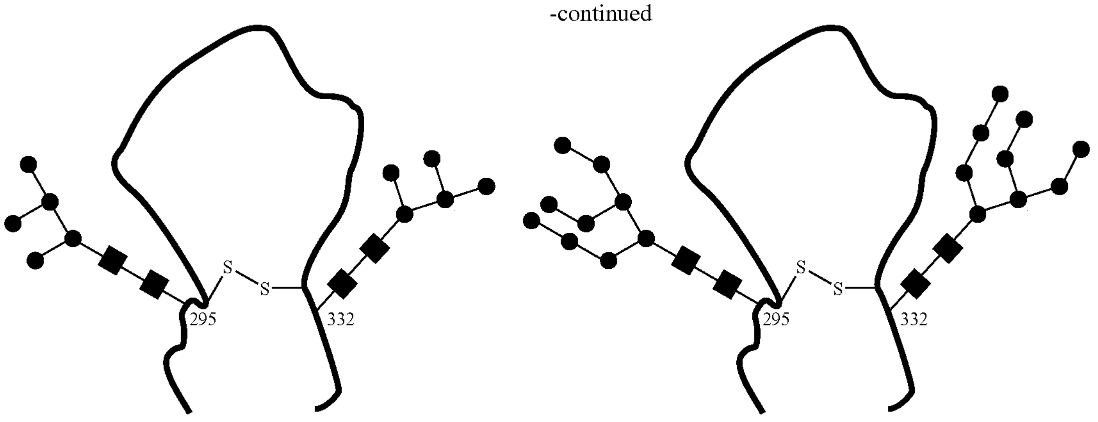

HB-V3-(G2M5)2 HB-V3-(G2M9)2

GlcNAc; Man; Gal

All the high-mannose type N-glycans, ranging from Man5 and Man6 to Man9, are actually present on HIV-1 gp120 [34-36].

Therefore, the synthetic glycopeptide variants are very useful for studying the relationships between the different glycoforms and their immunological properties.

Following the procedure for the synthesis of HXB2 V3-glycopeptides as described above, the corresponding BAL strain V3-glycopeptides (BAL gp$120^{291-336}$) is synthesized in the same way and used for immunological studies.

Importantly, it is theorized that the trivalent V3 glycopeptides possess unique immunological properties heretofore unknown. The synthesis of the V3 trivalent glycopeptides, however, requires a careful design of the conjugation chemistry. Usually, a synthetic peptide antigen would be conjugated to a scaffold or a carrier protein by the well-established thiol-maleimide reaction. However, since the cyclic V3 peptide contains a disulfide bond, introducing an additional free cysteine in the cyclic peptide may cause some problems, including possible thiol-disulfide shuffling and dimerization during enzymatic oligosaccharide transfer for the glycopeptide synthesis.

As such, the synthesis was accomplished by choosing a chemoselective ligation between an amino-oxy and an aldehyde functionality to form a stable oxime linkage.

There are a number of examples using the oxime chemistry to prepare large, protein-like molecules that are useful as artificial protein mimics and as peptide-based immunogens [145-152].

For such purpose, an aminooxy moiety is introduced at the N-terminus of the V3 GlcNAc-peptide during solid-phase peptide synthesis, using the Boc-protected aminooxyacetic acid (Boc-NH—O—$CH_2CO_2H$) as a building block for the last coupling step.

After the synthesis, the GlcNAc-peptide is retrieved from the resin with simultaneous side-chain deprotection by treatment with cocktail R (90:5:3:2, TFA-thioanisole-EDT-anisole) and 5% hydrazine.

Under these conditions, the Boc protecting group on the amino-oxy functionality is also removed to give the free aminooxy-containing GlcNAc-peptide, which likely are equally efficient for the subsequent enzymatic transglycosylation to form the desired aminooxy-containing glycopeptide.

As shown in Scheme 13, the chemoselective ligation between the free aminooxy-containing glycopeptide with the aldehyde-containing template is performed in a buffer (pH 3-5) according to the reported procedures [145, 148-152].

Scheme 13. Synthesis of trivalent V3 domain

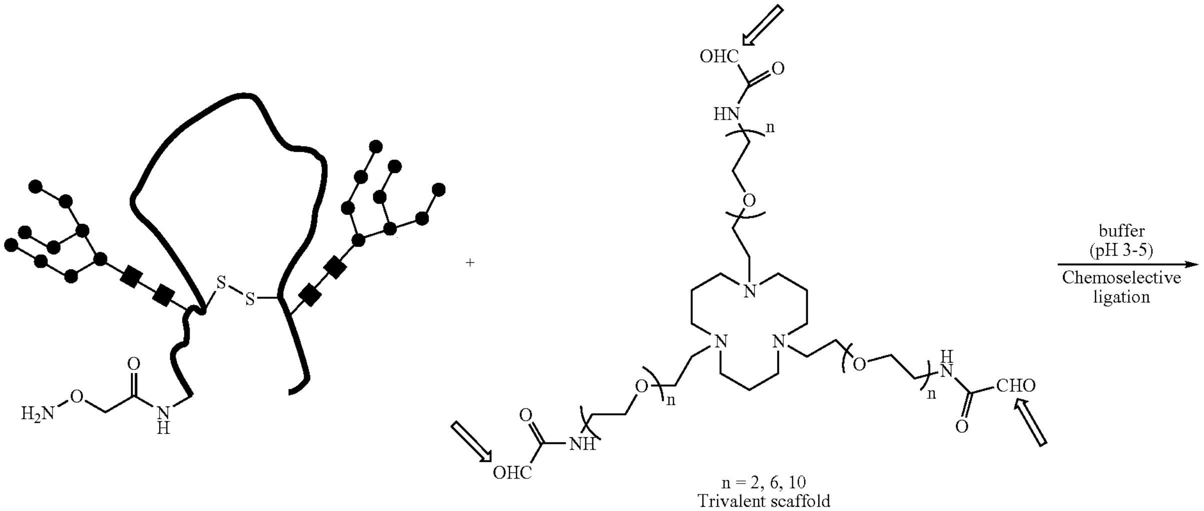

n = 2, 6, 10
Trivalent scaffold

-continued

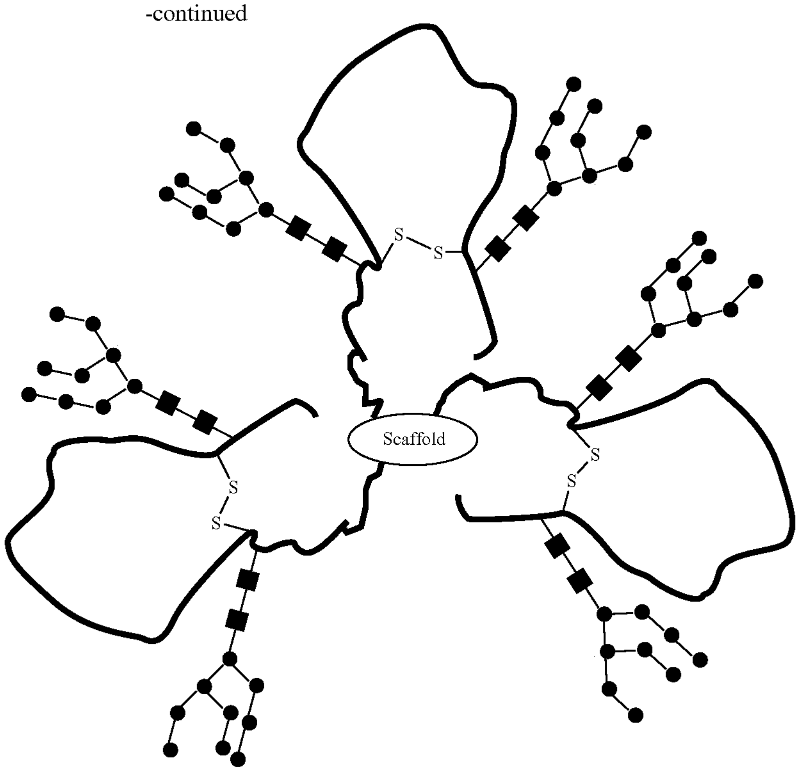

Trivalent V3 domain

The ligation is monitored by RP-HPLC. The reaction should be complete within several hours to one day, and the trivalent V3 glycopeptide will be purified by RP-HPLC and characterized by ESI-MS, amino acid analysis, and carbohydrate analysis.

By changing the length of the spacer in the scaffold, and/or changing the rigidity of the scaffold, it is possible to construct well defined molecules to mimic the 3D-orientation of the V3 domains present in the trimeric gp120 complex.

Thus, the present invention provides a method of making a synthetic glycopeptide, by addition of a synthetic oligosaccharide oxazoline to a GlcNAc-containing peptide precursor in the presence of an enzyme selected from among Endo-A and Endo-M. This method is readily employed to synthesize the aforementioned trivalent V3-domain glycopeptide including three V3-domain glycopeptides on a scaffold, wherein the three V3-domain glycopeptides are arranged to mimic the V3 domain presentation in trimeric gp120. The invention thereby enables trivalent V3-domain glycopeptides to be efficiently produced, e.g., for use in a vaccine for the treatment or prevention of HIV-1 infection.

REFERENCES

All contents of the references cited herein are incorporated by reference herein.

[1] Burton, D. R., Desrosiers, R. C., Doms, R. W., Koff, W. C., Kwong, P. D., Moore, J. P., Nabel, G. J., Sodroski, J., Wilson, I. A., and Wyatt, R. T. 2004. HIV vaccine design and the neutralizing antibody problem. Nat Immunol 5:233-236.

[2] Zolla-Pazner, S. 2004. Identifying epitopes of HIV-1 that induce protective antibodies. Nat Rev Immunol 4:199-210.

[3] Wyatt, R., Kwong, P. D., Desjardins, E., Sweet, R. W., Robinson, J., Hendrickson, W. A., and Sodroski, J. G. 1998. The antigenic structure of the HIV gp120 envelope glycoprotein. Nature 393:705-711.

[4] Trkola, A., Purtscher, M., Muster, T., Ballaun, C., Buchacher, A., Sullivan, N., Srinivasan, K., Sodroski, J., Moore, J. P., and Katinger, H. 1996. Human monoclonal antibody 2G 12 defines a distinctive neutralization epitope on the gp120 glycoprotein of human immunodeficiency virus type 1. J Virol 70:1100-1108.

[5] Scanlan, C. N., Pantophlet, R., Wormald, M. R., Ollmann Saphire, E., Stanfield, R., Wilson, I. A., Katinger, H., Dwek, R. A., Rudd, P. M., and Burton, D. R. 2002. The broadly neutralizing anti-human immunodeficiency virus type 1 antibody 2G 12 recognizes a cluster of alpha1->2 mannose residues on the outer face of gp120. J Virol 76:7306-7321.

[6] Sanders, R. W., Venturi, M., Schiffner, L., Kalyanaraman, R., Katinger, H., Lloyd, K. O., Kwong, P. D., and Moore, J. P. 2002. The mannose-dependent epitope for neutralizing antibody 2G 12 on human immunodeficiency virus type 1 glycoprotein gp120. J Virol 76:7293-7305.

[7] Danishefsky, S. J., and Allen, J. R. 2000. From the Laboratory to the Clinic: A Retrospective on Fully Synthetic Carbohydrate-Based Anticancer Vaccines Frequently used abbreviations are listed in the appendix. Angew Chem Int Ed 39:836-863.

[8] Imperiali, B., and Rickert, K. W. 1995. Conformational implications of asparagine-linked glycosylation. Proc Natl Acad Sci USA 92:97-101.

[9] Lisowska, E. 2002. The role of glycosylation in protein antigenic properties. Cell Mol Life Sci 59:445-455.

[10] Pantophlet, R., Wilson, I. A., and Burton, D. R. 2003. Hyperglycosylated mutants of human immunodeficiency virus (HIV) type 1 monomeric gp120 as novel antigens for HIV vaccine design. J Virol 77:5889-5901.

[11] Garrity, R. R., Rimmelzwaan, G., Minassian, A., Tsai, W. P., Lin, G., de Jong, J. J., Goudsmit, J., and Nara, P. L. 1997. Refocusing neutralizing antibody response by targeted dampening of an immunodominant epitope. J Immunol 159:279-289.

[12] UNAIDS. 2004. 2004 Report on the global AIDS epidemic. World Health Organization.

[13] Calarota, S. A., and Weiner, D. B. 2003. Present status of human HIV vaccine development. Aids 17 Suppl 4:S73-84.

[14] Nabel, G. J. 2001. Challenges and opportunities for development of an AIDS vaccine. Nature 410:1002-1007.

[15] McMichael, A. J., and Rowland-Jones, S. L. 2001. Cellular immnune responses to HIV. Nature 410:980-987.

[16] Burton, D. R. 2002. Antibodies, viruses and vaccines. Nat Rev Immunol 2:706-713.

[17] Emini, E. A., Schleif, W. A., Nunberg, J. H., Conley, A. J., Eda, Y., Tokiyoshi, S., Putney, S. D., Matsushita, S., Cobb, K. E., Jett, C. M., and et al. 1992. Prevention of HIV-1 infection in chimpanzees by gp120 V3 domain-specific monoclonal antibody. Nature 355:728-730.

[18] Shibata, R., Igarashi, T., Haigwood, N., Buckler-White, A., Ogert, R., Ross, W., Willey, R., Cho, M. W., and Martin, M. A. 1999. Neutralizing antibody directed against the HIV-1 envelope glycoprotein can completely block HIV-1/SIV chimeric virus infections of macaque monkeys. Nat Med 5:204-210.

[19] Mascola, J. R., Stiegler, G., VanCott, T. C., Katinger, H., Carpenter, C. B., Hanson, C. E., Beary, H., Hayes, D., Frankel, S. S., Birx, D. L., and Lewis, M. G. 2000. Protection of macaques against vaginal transmission of a pathogenic HIV-1/SIV chimeric virus by passive infusion of neutralizing antibodies. Nat Med 6:207-210.

[20] Baba, T. W., Liska, V., Hofmann-Lehmann, R., Vlasak, J., Xu, W., Ayehunie, S., Cavacini, L. A., Posner, M. R., Katinger, H., Stiegler, G., Bernacky, B. J., Rizvi, T. A., Schmidt, R., Hill, L. R., Keeling, M. E., Lu, Y., Wright, J. E., Chou, T. C., and Ruprecht, R. M. 2000. Human neutralizing monoclonal antibodies of the IgG1 subtype protect against mucosal simian-human immunodeficiency virus infection. Nat Med 6:200-206.

[21] Parren, P. W., Marx, P. A., Hessell, A. J., Luckay, A., Harouse, J., Cheng-Mayer, C., Moore, J. P., and Burton, D. R. 2001. Antibody protects macaques against vaginal challenge with a pathogenic R5 simian/human immunodeficiency virus at serum levels giving complete neutralization in vitro. J Virol 75:8340-8347.

[22] Chan, D. C., Fass, D., Berger, J. M., and Kim, P. S. 1997. Core structure of gp41 from the HIV envelope glycoprotein. Cell 89:263-273.

[23] Chan, D. C., and Kim, P. S. 1998. HIV entry and its inhibition. Cell 93:681-684.

[24] Saphire, E. O., Parren, P. W., Pantophlet, R., Zwick, M. B., Morris, G. M., Rudd, P. M., Dwek, R. A., Stanfield, R. L., Burton, D. R., and Wilson, I. A. 2001. Crystal structure of a neutralizing human IGG against HIV-1: a template for vaccine design. Science 293:1155-1159.

[25] Calarese, D. A., Scanlan, C. N., Zwick, M. B., Deechongkit, S., Mimura, Y., Kunert, R., Zhu, P., Wormald, M. R., Stanfield, R. L., Roux, K. H., Kelly, J. W., Rudd, P. M., Dwek, R. A., Katinger, H., Burton, D. R., and Wilson, I. A. 2003. Antibody domain exchange is an immunological solution to carbohydrate cluster recognition. Science 300:2065-2071.

[26] Parker, C. E., Deterding, L. J., Hager-Braun, C., Binley, J. M., Schulke, N., Katinger, H., Moore, J. P., and Tomer, K. B. 2001. Fine definition of the epitope on the gp41 glycoprotein of human immunodeficiency virus type 1 for the neutralizing monoclonal antibody 2F5. J Virol 75:10906-10911.

[27] Zwick, M. B., Labrijn, A. F., Wang, M., Spenlehauer, C., Saphire, E. O., Binley, J. M., Moore, J. P., Stiegler, G., Katinger, H., Burton, D. R., and Parren, P. W. 2001. Broadly neutralizing antibodies targeted to the membrane-proximal external region of human immunodeficiency virus type 1 glycoprotein gp41. J Virol 75:10892-10905.

[28] Ofek, G., Tang, M., Sambor, A., Katinger, H., Mascola, J. R., Wyatt, R., and Kwong, P. D. 2004. Structure and mechanistic analysis of the anti-human immunodeficiency virus type 1 antibody 2F5 in complex with its gp41 epitope. J Virol 78:10724-10737.

[29] Gorny, M. K., Williams, C., Volsky, B., Revesz, K., Cohen, S., Polonis, V. R., Honnen, W. J., Kayman, S. C., Krachmarov, C., Pinter, A., and Zolla-Pazner, S. 2002. Human monoclonal antibodies specific for conformation-sensitive epitopes of V3 neutralize human immunodeficiency virus type 1 primary isolates from various clades. J Virol 76:9035-9045.

[30] Varki, A. 1993. Biological roles of oligosaccharides: all of the theories are correct. Glycobiology 3:97-130.

[31] Dwek, R. A. 1996. Glycobiology: Toward understanding the function of sugars. Chem. Rev. 96:683-720.

[32] Rudd, P. M., Elliott, T., Cresswell, P., Wilson, I. A., and Dwek, R. A. 2001. Glycosylation and the immune system. Science 291:2370-2376.

[33] Helenius, A., and Aebi, M. 2001. Intracellular functions of N-linked glycans. Science 291:2364-2369.

[34] Mizuochi, T., Matthews, T. J., Kato, M., Hamako, J., Titani, K., Solomon, J., and Feizi, T. 1990. Diversity of oligosaccharide structures on the envelope glycoprotein gp 120 of human immunodeficiency virus 1 from the lymphoblastoid cell line H9. Presence of complex-type oligosaccharides with bisecting N-acetylglucosamine residues. J Biol Chem 265:8519-8524.

[35] Leonard, C. K., Spellman, M. W., Riddle, L., Harris, R. J., Thomas, J. N., and Gregory, T. J. 1990. Assignment of intrachain disulfide bonds and characterization of potential glycosylation sites of the type 1 recombinant human immunodeficiency virus envelope glycoprotein (gp120) expressed in Chinese hamster ovary cells. J Biol Chem 265:10373-10382.

[36] Zhu, X., Borchers, C., Bienstock, R. J., and Tomer, K. B. 2000. Mass spectrometric characterization of the glycosylation pattern of HIV-gp120 expressed in CHO cells. Biochemistry 39:11194-11204.

[37] Perrin, C., Fenouillet, E., and Jones, I. M. 1998. Role of gp41 glycosylation sites in the biological activity of human immunodeficiency virus type 1 envelope glycoprotein. Virology 242:338-345.

[38] Johnson, W. E., Sauvron, J. M., and Desrosiers, R. C. 2001. Conserved, N-linked carbohydrates of human immunodeficiency virus type 1 gp41 are largely dispensable for viral replication. J Virol 75:11426-11436.

[39] Kornfeld, R., and Kornfeld, S. 1985. Assembly of asparagine-linked oligosaccharides. Annu Rev Biochem 54:631-664.

[40] Reitter, J. N., Means, R. E., and Desrosiers, R. C. 1998. A role for carbohydrates in immune evasion in AIDS. Nat Med 4:679-684.

[41] Wei, X., Decker, J. M., Wang, S., Hui, H., Kappes, J. C., Wu, X., Salazar-Gonzalez, J. F., Salazar, M. G., Kilby, J. M., Saag, M. S., Komarova, N. L., Nowak, M. A., Hahn, B. H., Kwong, P. D., and Shaw, G. M. 2003. Antibody neutralization and escape by HIV-1. Nature 422:307-312.

[42] Back, N. K., Smit, L., De Jong, J. J., Keulen, W., Schutten, M., Goudsmit, J., and Tersmette, M. 1994. An N-glycan within the human immunodeficiency virus type 1 gp120 V3 loop affects virus neutralization. Virology 199: 431-438.

[43] Ly, A., and Stamatatos, L. 2000. V2 loop glycosylation of the human immunodeficiency virus type 1 SF162 envelope facilitates interaction of this protein with CD4 and CCR5 receptors and protects the virus from neutralization by anti-V3 loop and anti-CD4 binding site antibodies. J Virol 74:6769-6776.

[44] Koch, M., Pancera, M., Kwong, P. D., Kolchinsky, P., Grundner, C., Wang, L., Hendrickson, W. A., Sodroski, J., and Wyatt, R. 2003. Structure-based, targeted deglycosylation of HIV-1 gp120 and effects on neutralization sensitivity and antibody recognition. Virology 313:387-400.

[45] Malenbaum, S. E., Yang, D., Cavacini, L., Posner, M., Robinson, J., and Cheng-Mayer, C. 2000. The N-terminal V3 loop glycan modulates the interaction of clade A and B human immunodeficiency virus type 1 envelopes with CD4 and chemokine receptors. J Virol 74:11008-11016.

[46] Grundner, C., Pancera, M., Kang, J. M., Koch, M., Sodroski, J., and Wyatt, R. 2004. Factors limiting the immunogenicity of HIV-1 gp120 envelope glycoproteins. Virology 330:233-248.

[47] McCaffrey, R. A., Saunders, C., Hensel, M., and Stamatatos, L. 2004. N-linked glycosylation of the V3 loop and the immunologically silent face of gp120 protects human immunodeficiency virus type 1 SF162 from neutralization by anti-gp120 and anti-gp41 antibodies. J Virol 78:3279-3295.

[48] Kang, S. M., Shi Quan, F., Huang, C., Guo, L., Ye, L., Yang, C., and Compans, R. W. 2005. Modified HIV envelope proteins with enhanced binding to neutralizing monoclonal antibodies. Virology 331:20-32.

[49] Quinones-Kochs, M. I., Buonocore, L., and Rose, J. K. 2002. Role of N-linked glycans in a human immunodeficiency virus envelope glycoprotein: effects on protein function and the neutralizing antibody response. J Virol 76:4199-4211.

[50] Cole, K. S., Steckbeck, J. D., Rowles, J. L., Desrosiers, R. C., and Montelaro, R. C. 2004. Removal of N-linked glycosylation sites in the V1 region of simian immunodeficiency virus gp120 results in redirection of B-cell responses to V3. J Virol 78:1525-1539.

[51] Delves, P. J., Lund, T., and Roitt, I. M. 1997. Can epitope-focused vaccines select advantageous immune responses? Mol Med Today 3:55-60.

[52] Pantophlet, R., and Burton, D. R. 2003. Immunofocusing: antigen engineering to promote the induction of HIV-neutralizing antibodies. Trends Mol Med 9:468-473.

[53] Otvos, L., Jr., and Cudic, M. 2003. Conformation of glycopeptides. Mini Rev Med Chem 3:703-711.

[54] O'Connor, S. E., and Imperiali, B. 1996. Modulation of protein structure and function by asparagine-linked glycosylation. Chem Biol 3:803-812.

[55] Imperiali, B., and O'Connor, S. E. 1999. Effect of N-linked glycosylation on glycopeptide and glycoprotein structure. Curr. Opin. Chem. Biol. 3:643-649.

[56] Imperiali, B., and Hendrickson, T. L. 1995. Asparagine-linked glycosylation: specificity and function of oligosaccharyl transferase. Bioorg Med Chem 3:1565-1578.

[57] Andreotti, A. H., and Kahne, D. 1993. Effects of glycosylation on peptide backbone conformation. J. Am. Chem. Soc. 115:3352-3353.

[58] Liang, R., Andreotti, A. H., and Kahne, D. 1995. Sensitivity of glycopeptide conformation to carbohydrate chain length. J. Am. Chem. Soc. 117:10395-10396.

[59] O'Conner, S. E., and Imperiali, B. 1998. A molecular basis for glycosylation-induced conformational switching. Chem Biol 5:427-437.

[60] O'Connor, S. E., Pohlmann, J., Imperiali, B., Saskiawan, I., and Yamamoto, K. 2001. Probing the effect of the outer saccharide residues of N-linked glycans on peptide conformation. J Am Chem Soc 123:6187-6188.

[61] Bosques, C. J., Tschampel, S. M., Woods, R. J., and Imperiali, B. 2004. Effects of glycosylation on peptide conformation: a synergistic experimental and computational study. J Am Chem Soc 126:8421-8425.

[62] Vranken, W. F., Budesinsky, M., Martins, J. C., Fant, F., Boulez, K., Gras-Masse, H., and Borremans, F. A. 1996. Conformational features of a synthetic cyclic peptide corresponding to the complete V3 loop of the RF HIV-1 strain in water and water/trifluoroethanol solutions. Eur J Biochem 236:100-108.

[63] Gupta, G., Anantharamaiah, G. M., Scott, D. R., Eldridge, J. H., and Myers, G. 1993. Solution structure of the V3 loop of a Thailand HIV isolate. J Biomol Struct Dyn 11:345-366.

[64] Vranken, W. F., Fant, F., Budesinsky, M., and Borremans, F. A. 2001. Conformational model for the consensus V3 loop of the envelope protein gp120 of HIV-1 in a 20% trifluoroethanol/water solution. Eur J Biochem 268:2620-2628.

[65] Vranken, W. F., Budesinsky, M., Fant, F., Boulez, K., and Borremans, F. A. 1995. The complete Consensus V3 loop peptide of the envelope protein gp120 of HIV-1 shows pronounced helical character in solution. FEBS Lett 374: 117-121.

[66] Catasti, P., Bradbury, E. M., and Gupta, G. 1996. Structure and polymorphism of HIV-1 third variable loops. J Biol Chem 271:8236-8242.

[67] Catasti, P., Fontenot, J. D., Bradbury, E. M., and Gupta, G. 1995. Local and global structural properties of the HIV-MN V3 loop. J Biol Chem 270:2224-2232.

[68] Campbell, A. P., Sykes, B. D., Norrby, E., Assa-Munt, N., and Dyson, H. J. 1996. Solution conformation of an immunogenic peptide derived from the principal neutralizing determinant of the HIV-2 envelope glycoprotein gp125. Fold Des 1:157-165.

[69] Ghiara, J. B., Ferguson, D. C., Satterthwait, A. C., Dyson, H. J., and Wilson, I. A. 1997. Structure-based design of a constrained peptide mimic of the HIV-1 V3 loop neutralization site. J Mol Biol 266:31-39.

[70] Zvi, A., Feigelson, D. J., Hayek, Y., and Anglister, J. 1997. Conformation of the principal neutralizing determinant of human immunodeficiency virus type 1 in complex with an anti-gp120 virus neutralizing antibody studied by two-dimensional nuclear magnetic resonance difference spectroscopy. Biochemistry 36:8619-8627.

[71] Cabezas, E., Wang, M., Parren, P. W., Stanfield, R. L., and Satterthwait, A. C. 2000. A structure-based approach to a synthetic vaccine for HIV-1. Biochemistry 39:14377-14391.

[72] Tugarinov, V., Zvi, A., Levy, R., Hayek, Y., Matsushita, S., and Anglister, J. 2000. NMR structure of an anti-gp120 antibody complex with a V3 peptide reveals a surface important for co-receptor binding. Structure Fold Des 8:385-395.

[73] Andrianov, A. M. 2002. Local structural properties of the V3 loop of Thailand HIV-1 isolate. J Biomol Struct Dyn 19:973-989.

[74] Andrianov, A. M. 2004. Dual spatial folds and different local structures of the HIV-1 immunogenic crown in various virus isolates. J Biomol Struct Dyn 22:159-170.

[75] Rini, J. M., Stanfield, R. L., Stura, E. A., Salinas, P. A., Profy, A. T., and Wilson, I. A. 1993. Crystal structure of a human immunodeficiency virus type 1 neutralizing antibody, 50.1, in complex with its V3 loop peptide antigen. Proc Natl Acad Sci USA 90:6325-6329.

[76] Ghiara, J. B., Stura, E. A., Stanfield, R. L., Profy, A. T., and Wilson, I. A. 1994. Crystal structure of the principal neutralization site of HIV-1. Science 264:82-85.

[77] Stanfield, R. L., Ghiara, J. B., Ollmann Saphire, E., Profy, A. T., and Wilson, I. A. 2003. Recurring conformation of the human immunodeficiency virus type 1 gp120 V3 loop. Virology 315:159-173.

[78] Stanfield, R. L., Gorny, M. K., Williams, C., Zolla-Pazner, S., and Wilson, I. A. 2004. Structural rationale for the broad neutralization of HIV-1 by human monoclonal antibody 447-52D. Structure (Camb) 12:193-204.

[79] Laczko, I., Hollosi, M., Urge, L., Ugen, K. E., Weiner, D. B., Mantsch, H. H., Thurin, J., and Otvos, L., Jr. 1992. Synthesis and conformational studies of N-glycosylated analogues of the HIV-1 principal neutralizing determinant. Biochemistry 31:4282-4288.

[80] Huang, X., Smith, M. C., Berzofsky, J. A., and Barchi, J. J., Jr. 1996. Structural comparison of a 15 residue peptide from the V3 loop of HIV-1IIIb and an O-glycosylated analogue. FEBS Lett 393:280-286.

[81] Huang, X., Barchi, J. J., Jr., Lung, F. D., Roller, P. P., Nara, P. L., Muschik, J., and Garrity, R. R. 1997. Glycosylation affects both the three-dimensional structure and antibody binding properties of the HIV-1 IIIB GP120 peptide RP135. Biochemistry 36:10846-10856.

[82] Chen, B., Vogan, E. M., Gong, H., Skehel, J. J., Wiley, D. C., and Harrison, S. C. 2005. Structure of an unliganded simian immunodeficiency virus gp120 core. Nature 433: 834-841.

[83] Chen, B., Vogan, E. M., Gong, H., Skehel, J. J., Wiley, D. C., and Harrison, S. C. 2005. Determining the structure of an unliganded and fully glycosylated SIV gp120 envelope glycoprotein. Structure (Camb) 13:197-211.

[84] Kwong, P. D., Wyatt, R., Robinson, J., Sweet, R. W., Sodroski, J., and Hendrickson, W. A. 1998. Structure of an HIV gp120 envelope glycoprotein in complex with the CD4 receptor and a neutralizing human antibody. Nature 393:648-659.

[85] Hartley, O., Klasse, P. J., Sattentau, Q. J., and Moore, J. P. 2005. V3: HIV's switch-hitter. AIDS Res Hum Retroviruses 21:171-189.

[86] Gorny, M. K., Conley, A. J., Karwowska, S., Buchbinder, A., Xu, J. Y., Emini, E. A., Koenig, S., and Zolla-Pazner, S. 1992. Neutralization of diverse human immunodeficiency virus type 1 variants by an anti-V3 human monoclonal antibody. J Virol 66:7538-7542.

[87] Conley, A. J., Gorny, M. K., Kessler, J. A., 2nd, Boots, L. J., Ossorio-Castro, M., Koenig, S., Lineberger, D. W., Emini, E. A., Williams, C., and Zolla-Pazner, S. 1994. Neutralization of primary human immunodeficiency virus type 1 isolates by the broadly reactive anti-V3 monoclonal antibody, 447-52D. J Virol 68:6994-7000.

[88] Krachmarov, C. P., Kayman, S. C., Honnen, W. J., Trochev, O., and Pinter, A. 2001. V3-specific polyclonal antibodies affinity purified from sera of infected humans effectively neutralize primary isolates of human immunodeficiency virus type 1. AIDS Res Hum Retroviruses 17:1737-1748.

[89] Zolla-Pazner, S., Zhong, P., Revesz, K., Volsky, B., Williams, C., Nyambi, P., and Gorny, M. K. 2004. The Cross-Clade Neutralizing Activity of a Human Monoclonal Antibody Is Determined by the GPGR V3 Motif of HIV Type 1. AIDS Res Hum Retroviruses 20:1254-1258.

[90] White-Scharf, M. E., Potts, B. J., Smith, L. M., Sokolowski, K. A., Rusche, J. R., and Silver, S. 1993. Broadly neutralizing monoclonal antibodies to the V3 region of HIV-1 can be elicited by peptide immunization. Virology 192:197-206.

[91] Gorny, M. K., Revesz, K., Williams, C., Volsky, B., Louder, M. K., Anyangwe, C. A., Krachmarov, C., Kayman, S. C., Pinter, A., Nadas, A., Nyambi, P. N., Mascola, J. R., and Zolla-Pazner, S. 2004. The v3 loop is accessible on the surface of most human immunodeficiency virus type 1 primary isolates and serves as a neutralization epitope. J Virol 78:2394-2404.

[92] Zolla-Pazner, S., Gomy, M. K., and Nyambi, P. N. 1999. The implications of antigenic diversity for vaccine development. Immunol Lett 66:159-164.

[93] Stanfield, R., Cabezas, E., Satterthwait, A., Stura, E., Profy, A., and Wilson, I. 1999. Dual conformations for the HIV-1 gp120 V3 loop in complexes with different neutralizing fabs. Structure Fold Des 7:131-142.

[94] Kwong, P. D., Wyatt, R., Sattentau, Q. J., Sodroski, J., and Hendrickson, W. A. 2000. Oligomeric modeling and electrostatic analysis of the gp120 envelope glycoprotein of human immunodeficiency virus. J Virol 74:1961-1972.

[95] LaRosa, G. J., Davide, J. P., Weinhold, K., Waterbury, J. A., Profy, A. T., Lewis, J. A., Langlois, A. J., Dreesman, G. R., Boswell, R. N., Shadduck, P., and et al. 1990. Conserved sequence and structural elements in the HIV-1 principal neutralizing determinant. Science 249:932-935.

[96] Hoffman, T. L., and Doms, R. W. 1999. HIV-1 envelope determinants for cell tropism and chemokine receptor use. Mol Membr Biol 16:57-65.

[97] Rizzuto, C. D., Wyatt, R., Hernandez-Ramos, N., Sun, Y., Kwong, P. D., Hendrickson, W. A., and Sodroski, J. 1998. A conserved HIV gp120 glycoprotein structure involved in chemokine receptor binding. Science 280:1949-1953.

[98] Rizzuto, C., and Sodroski, J. 2000. Fine definition of a conserved CCR5-binding region on the human immunodeficiency virus type 1 glycoprotein 120. AIDS Res Hum Retroviruses 16:741-749.

[99] Basmaciogullari, S., Babcock, G. J., Van Ryk, D., Wojtowicz, W., and Sodroski, J. 2002. Identification of conserved and variable structures in the human immunodeficiency virus gp120 glycoprotein of importance for CXCR4 binding. J Virol 76:10791-10800.

[100] Sharon, M., Kessler, N., Levy, R., Zolla-Pazner, S., Gorlach, M., and Anglister, J. 2003. Alternative conformations of HIV-1 V3 loops mimic beta hairpins in chemokines, suggesting a mechanism for coreceptor selectivity. Structure (Camb) 11:225-236.

[101] Yonezawa, A., Hori, T., Takaori-Kondo, A., Morita, R., and Uchiyama, T. 2001. Replacement of the V3 region of gp120 with SDF-1 preserves the infectivity of T-cell line-tropic human immunodeficiency virus type 1. J Virol 75:4258-4267.

[102] Nardelli, B., Lu, Y. A., Shiu, D. R., Delpierre-Defoort, C., Profy, A. T., and Tam, J. P. 1992. A chemically defined synthetic vaccine model for HIV-1. J Immunol 148:914-920.

[103] Okuda, K., Kaneko, T., Yamakawa, T., Tanaka, S., Shigematsu, T., Yamamoto, A., Hamajima, K., Nakajima, K., Kawamoto, S., and Phanuphak, P. 1993. Strong immunogenicity of a multicomponent peptide vaccine developed with the branched lysine oligopeptide method for human immunodeficiency virus infection. J Mol Recognit 6:101-109.

[104] Liao, H. X., Etemad-Moghadam, B., Montefiori, D. C., Sun, Y., Sodroski, J., Scearce, R. M., Doms, R. W., Thomasch, J. R., Robinson, S., Letvin, N. L., and Haynes, B. F. 2000. Induction of antibodies in guinea pigs and rhesus monkeys against the human immunodeficiency virus type 1 envelope: neutralization of nonpathogenic and pathogenic primary isolate simian/human immunodeficiency virus strains. J Virol 74:254-263.

[105] Rubinstein, A., Mizrachi, Y., Pettoello-Mantovani, M., Lenz, J., Liu, G. Q., Rubinstein, Y., Goldstein, H., Yust, I., Burke, M., Vardinon, N., Spirer, Z., and Cryz, S. J., Jr. 1999. Immunologic responses of HIV-1-infected study subjects to immunization with a mixture of peptide protein derivative-V3 loop peptide conjugates. J Acquir Immune Defic Syndr 22:467-476.

[106] Tian, H., Xiao, Y., Zhu, M., and Chen, Y. H. 2001. HIV epitope-peptides in aluminum adjuvant induced high levels of epitope-specific antibodies. Int Immunopharmacol 1:763-768.

[107] Wang, L. X., Ni, J., Singh, S., and Li, H. 2004. Binding of high-mannose-type oligosaccharides and synthetic oligomannose clusters to human antibody 2G12: implications for HIV-1 vaccine design. Chem Biol 11:127-134.

[108] Li, H., and Wang, L. X. 2004. Design and synthesis of a template-assembled oligomannose cluster as an epitope mimic for human HIV-neutralizing antibody 2G12. Org Biomol Chem 2:483-488.

[109] Kudryashov, V., Glunz, P. W., Williams, L. J., Hintermann, S., Danishefsky, S. J., and Lloyd, K. O. 2001. Toward optimized carbohydrate-based anticancer vaccines: epitope clustering, carrier structure, and adjuvant all influence antibody responses to Lewis(y) conjugates in mice. Proc Natl Acad Sci USA 98:3264-3269.

[110] Arsequell, G., and Valencia, G. 1999. Recent advances in the synthesis of complex N-glycopeptides. Tetrahedron: Asymmetry 10:3045-3094.

[111] Meldal, M., and St Hilaire, P. M. 1997. Synthetic methods of glycopeptide assembly, and biological analysis of glycopeptide products. Curr. Opin. Chem. Biol. 1:552-563.

[112] Meldal, M., and Bock, K. 1994. A general approach to the synthesis of O- and N-linked glycopeptides. Glycoconjugate J. 11:59-63.

[113] Grogan, M. J., Pratt, M. R., Marcaurelle, L. A., and Bertozzi, C. R. 2002. Homogeneous glycopeptides and glycoproteins for biological investigation. Annu. Rev. Biochem. 71:593-634.

[114] Sears, P., and Wong, C. H. 2001. Toward automated synthesis of oligosaccharides and glycoproteins. Science 291:2344-2350.

[115] Yamamoto, K. 2001. Chemoenzymatic synthesis of bioactive glycopeptide using microbial endoglycosidase. J. Biosci. Bioeng. 92:493-501.

[116] Wang, L. X., Singh, S., and Ni, J. 2004. Synthesis of bioactive glycopeptides through endoglycosidase-catalyzed transgylcosylation, p. 73-92. In P. G. Wang and Y. Ichikawa (ed.), Synthesis of Carbohydrates through Biotechnology. American Chemical Society, Washington, D.C.

[117] Wang, L. X., Tang, M., Suzuki, T., Kitajima, K., Inoue, Y., Inoue, S., Fan, J. Q., and Lee, Y. C. 1997. Combined chemical and enzymic synthesis of a C-glycopeptide and its inhibitory activity toward glycoamidases. J. Am. Chem. Soc. 119:11137-11146.

[118] Yamamoto, K., and Takegawa, K. 1997. Transglycosylation activity of endoglycosidases and its application. Trends in Glycoscience and Glycotechnology 9:339-354.

[119] Mizuno, M., Haneda, K., Iguchi, R., Muramoto, I., Kawakami, T., Aimoto, S., Yamamoto, K., and Inazu, T. 1999. Synthesis of a glycopeptide containing oligosaccharides: chemoenzymatic synthesis of eel calcitonin analogues having natural N-linked oligosaccharides. J. Am. Chem. Soc. 121:284-290.

[120] Wang, L. X., Fan, J. Q., and Lee, Y. C. 1996. Chemoenzymatic synthesis of a high-mannose type N-glycopeptide analog with C-glycosidic linkage. Tetrahedron Lett. 37:1975-1978.

[121] Yamamoto, K., Fujimori, K., Haneda, K., Mizuno, M., Inazu, T., and Kumagai, H. 1998. Chemoenzymatic synthesis of a novel glycopeptide using a microbial endoglycosidase. Carbohydr. Res. 305:415-422.

[122] Takegawa, K., Fujita, K., Fan, J. Q., Tabuchi, M., Tanaka, N., Kondo, A., Iwamoto, H., Kato, I., Lee, Y. C., and Iwahara, S. 1998. Enzymatic synthesis of a neoglycoconjugate by transglycosylation with *Arthrobacter* endo-beta-N-acetylglucosaminidase: a substrate for colorimetric detection of endo-beta-N-acetylglucosaminidase activity. Anal. Biochem. 257:218-223.

[123] Singh, S., Ni, J., and Wang, L. X. 2003. Chemoenzymatic synthesis of high-mannose type HIV-1 gp120 glycopeptides. Bioorg Med Chem Lett 13:327-330.

[124] Li, H., Singh, S., Zeng, Y., Song, H., and Wang, L. X. 2005. Chemoenzymatic synthesis of CD52 glycoproteins carrying native N-glycans. Bioorg Med Chem Lett 15:895-898.

[125] Wang, L. X., Song, H., Liu, S., Lu, H., Jiang, S., Ni, J., and Li, H. 2005. Chemoenzymatic synthesis of HIV-1 glycopeptides. Effects of glycosylation on the antiviral activity and alpha-helix bundle-forming ability of gp41 peptide C34. ChemBioChem in press.

[126] Seko, A., Koketsu, M., Nishizono, M., Enoki, Y., Ibrahim, H. R., Juneja, L. R., Kim, M., and Yamamoto, T. 1997. Occurence of a sialylglycopeptide and free sialylglycans in hen's egg yolk. Biochim Biophys Acta 1335:23-32.

[127] Huang, C. C., Mayer, H. E., and Montgomery, R. 1970. Microheterogeneity and paucidispersity of glycoproteins. Part I. The carbohydrate of chicken ovalbumin. Carbohydrate Research 13:127-137.

[128] Colon, M., Staveski, M. M., and Davis, J. T. 1991. Mild conditions for the preparation of high-mannose oligosaccharide oxazolines: entry point for beta-glycoside and neoglycoprotein syntheses. Tetrahedron Lett. 32:4447-4450.

[129] Fan, J. Q., Takegawa, K., Iwahara, S., Kondo, A., Kato, I., Abeygunawardana, C., and Lee, Y. C. 1995. Enhanced transglycosylation activity of *Arthrobacter* protophormiae endo-beta-N-acetylglucosaminidase in media containing organic solvents. J. Biol. Chem. 270:17723-17729.

[130] Geng, X., Dudkin, V. Y., Mandal, M., and Danishefsky, S. J. 2004. In Pursuit of Carbohydrate-Based HIV Vaccines, Part 2: The Total Synthesis of High-Mannose-Type gp120 Fragments-Evaluation of Strategies Directed to Maximal Convergence. Angew Chem Int Ed 43:2562-2565.

[131] Mandal, M., Dudkin, V. Y., Geng, X., and Danishefsky, S. J. 2004. In Pursuit of Carbohydrate-Based HIV Vaccines, Part 1: The Total Synthesis of Hybrid-Type gp120 Fragments. Angew Chem Int Ed 43:2557-2561.

[132] Chittur, K. K. 1998. FTIR/ATR for protein adsorption to biomaterial surfaces. Biomaterials 19:357-369.

[133] Vigano, C., Manciu, L., Buyse, F., Goormaghtigh, E., and Ruysschaert, J. M. 2000. Attenuated total reflection IR spectroscopy as a tool to investigate the structure, orientation and tertiary structure changes in peptides and membrane proteins. Biopolymers 55:373-380.

[134] Morikawa, Y., Barsov, E., and Jones, I. 1993. Legitimate and illegitimate cleavage of human immunodeficiency virus glycoproteins by furin. J Virol 67:3601-3604.

[135] Brakch, N., Dettin, M., Scarinci, C., Seidah, N. G., and Di Bello, C. 1995. Structural investigation and kinetic characterization of potential cleavage sites of HIV GP160 by human furin and PC1. Biochem Biophys Res Commun 213:356-361.

[136] Vollenweider, F., Benjannet, S., Decroly, E., Savaria, D., Lazure, C., Thomas, G., Chretien, M., and Seidah, N. G. 1996. Comparative cellular processing of the human immunodeficiency virus (HIV-1) envelope glycoprotein gp160 by the mammalian subtilisin/kexin-like convertases. Biochem J 314:521-532.

[137] Geyer, H., Holschbach, C., Hunsmann, G., and Schneider, J. 1988. Carbohydrates of human immunodeficiency virus. Structures of oligosaccharides linked to the envelope glycoprotein 120. J Biol Chem 263:11760-11767.

[138] Ni, J., Powell, R., Baskakov, I. V., DeVico, A., Lewis, G. K., and Wang, L. X. 2004. Synthesis, conformation, and immunogenicity of monosaccharide-centered multivalent HIV-1 gp41 peptides containing the sequence of DP178. Bioorg Med Chem 12:3141-3148.

[139] Tam, J. P. 1996. Recent advances in multiple antigen peptides. J. Immunol. Methods 196:17-32.

[140] Wang, L. X., Ni, J., and Singh, S. 2003. Carbohydrate-centered maleimide cluster as new types of templates for multivalent peptide assembling: Synthesis of multivalent HIV-1 gp41 peptides. Bioorg. Med. Chem. 11:129-136.

[141] Ni, J., Singh, S., and Wang, L. X. 2003. Synthesis of maleimide-activated carbohydrates as chemoselective tags for site-specific glycosylation of peptides and proteins. Bioconjug Chem 14:232-238.

[142] Li, H., and Wang, L. X. 2003. Cholic acid as template for multivalent peptide assembly. Org Biomol Chem 1:3507-3513.

[143] Naicker, K. P., Li, H., Heredia, A., Song, H., and Wang, L. X. 2004. Design and synthesis of alpha Gal-conjugated peptide T20 as novel antiviral agent for HIV-immunotargeting. Org Biomol Chem 2:660-664.

[144] Li, H., Song, H., Heredia, A., Le, N., Redfield, R., Lewis, G. K., and Wang, L. X. 2004. Synthetic bivalent CD4-mimetic miniproteins show enhanced anti-HIV activity over the monovalent miniprotein. Bioconjug Chem 15:783-789.

[145] Shao, J., and Tam, J. P. 1995. Unprotected peptides as building blocks for the synthesis of peptide dendrimers with oxime, hydrazone, and thiazolidine linkages. J. Am. Chem. Soc. 117:3893-3899.

[146] Rose, K. 1994. Facile synthesis of homogeneous artificial proteins. J. Am. Chem. Soc. 116:30-33.

[147] Rose, K., Zeng, W., Brown, L. E., and Jackson, D. C. 1995. A synthetic peptide-based polyoxime vaccine construct of high purity and activity. Mol Immunol 32:1031-1037.

[148] Zeng, W., Jackson, D. C., and Rose, K. 1996. Synthesis of a new template with a built-in adjuvant and its use in constructing peptide vaccine candidates through polyoxime chemistry. J Pept Sci 2:66-72.

[149] Rose, K., Zeng, W., Regamey, P. O., Chernushevich, I. V., Standing, K. G., and Gaertner, H. F. 1996. Natural peptides as building blocks for the synthesis of large protein-like molecules with hydrazone and oxime linkages. Bioconjug Chem 7:552-556.

[150] Nardin, E. H., Calvo-Calle, J. M., Oliveira, G. A., Clavijo, P., Nussenzweig, R., Simon, R., Zeng, W., and Rose, K. 1998. Plasmodium falciparum polyoximes: highly immunogenic synthetic vaccines constructed by chemoselective ligation of repeat B-cell epitopes and a universal T-cell epitope of CS protein. Vaccine 16:590-600.

[151] Zeng, W., Jackson, D. C., Murray, J., Rose, K., and Brown, L. E. 2000. Totally synthetic lipid-containing polyoxime peptide constructs are potent immunogens. Vaccine 18:1031-1039.

[152] Chen, J., Zeng, W., Offord, R., and Rose, K. 2003. A novel method for the rational construction of well-defined immunogens: the use of oximation to conjugate cholera toxin B subunit to a peptide-polyoxime complex. Bioconjug Chem 14:614-618.

[153] Fagerstam, L. G., Frostell, A., Karlsson, R., Kullman, M., Larsson, A., Malmqvist, M., and Butt, H. 1990. Detection of antigen-antibody interactions by surface plasmon resonance. Application to epitope mapping. J Mol Recognit 3:208-214.

[154] Wu, G., MacKenzie, R., Durda, P. J., and Tsang, P. 2000. The binding of a glycoprotein 120 V3 loop peptide to HIV-1 neutralizing antibodies. Structural implications. J Biol Chem 275:36645-36652.

[155] Coeffier, E., Clement, J. M., Cussac, V., Khodaei-Boorane, N., Jehanno, M., Rojas, M., Dridi, A., Latour, M., El Habib, R., Barre-Sinoussi, F., Hofnung, M., and Leclerc, C. 2001. Antigenicity and immunogenicity of the HIV-1 gp41 epitope ELDKWA inserted into permissive sites of the MalE protein. Vaccine 19:684-693.

[156] Dudkin, V. Y., Orlova, M., Geng, X., Mandal, M., Olson, W. C., and Danishefsky, S. J. 2004. Toward fully synthetic carbohydrate-based HIV antigen design: on the critical role of bivalency. J Am Chem Soc 126:9560-9562.

[157] Fouts, T., Godfrey, K., Bobb, K., Montefiori, D., Hanson, C. V., Kalyanaraman, V. S., DeVico, A., and Pal, R. 2002. Crosslinked HIV-1 envelope-CD4 receptor complexes elicit broadly cross-reactive neutralizing antibodies in rhesus macaques. Proc Natl Acad Sci USA 99:11842-11847.

[158] DeVico, A., Silver, A., Thronton, A. M., Sarngadharan, M. G., and Pal, R. 1996. Covalently crosslinked complexes of human immunodeficiency virus type 1 (HIV-1) gp120 and CD4 receptor elicit a neutralizing immune response that includes antibodies selective for primary virus isolates. Virology 218:258-263.

[159] Vogel, T., Kurth, R., and Norley, S. 1994. The majority of neutralizing Abs in HIV-1-infected patients recognize linear V3 loop sequences. Studies using HIV-1 MN multiple antigenic peptides. J Immunol 153:1895-1904.

[160] Smith, D. E., O'Brien, M. E., Palmer, V. J., and Sadowski, J. A. 1992. The selection of an adjuvant emulsion for polyclonal antibody production using a low-molecular-weight antigen in rabbits. Lab Anim Sci 42:599-601.

[161] Johnson, D. A., Sowell, C. G., Johnson, C. L., Livesay, M. T., Keegan, D. S., Rhodes, M. J., Ulrich, J. T., Ward, J. R., Cantrell, J. L., and Brookshire, V. G. 1999. Synthesis and biological evaluation of a new class of vaccine adjuvants: aminoalkyl glucosaminide 4-phosphates (AGPs). Bioorg Med Chem Lett 9:2273-2278.

[162] Vogel, F. R. 1995. The role of adjuvants in retroviral vaccines. Int J Immunopharmacol 17:85-90.

[163] Griffiths, J. C., Berrie, E. L., Holdsworth, L. N., Moore, J. P., Harris, S. J., Senior, J. M., Kingsman, S. M., Kingsman, A. J., and Adams, S. E. 1991. Induction of high-titer neutralizing antibodies, using hybrid human immunodeficiency virus V3-Ty virus like particles in a clinically relevant adjuvant. J Virol 65:450-456.

[164] Raya, N. E., Quintana, D., Carrazana, Y., Gomez, C. E., and Duarte, C. A. 1999. A prime-boost regime that combines Montanide ISA720 and Alhydrogel to induce antibodies against the HIV-1 derived multiepitope polypeptide TAB9. Vaccine 17:2646-2650.

[165] Goudsmit, J., Debouck, C., Meloen, R. H., Smit, L., Bakker, M., Asher, D. M., Wolff, A. V., Gibbs, C. J., Jr., and Gajdusek, D. C. 1988. Human immunodeficiency virus type 1 neutralization epitope with conserved architecture elicits early type-specific antibodies in experimentally infected chimpanzees. Proc Natl Acad Sci USA 85:4478-4482.

[166] Andris, J. S., Johnson, S., Zolla-Pazner, S., and Capra, J. D. 1991. Molecular characterization of five human anti-human immunodeficiency virus type 1 antibody heavy chains reveals extensive somatic mutation typical of an antigen-driven immune response. Proc Natl Acad Sci USA 88:7783-7787.

[167] DeVico, A. L., Rahman, R., Welch, J., Crowley, R., Lusso, P., Sarngadharan, M. G., and Pal, R. 1995. Monoclonal antibodies raised against covalently crosslinked complexes of human immunodeficiency virus type 1 gp120 and CD4 receptor identify a novel complex-dependent epitope on gp120. Virology 211:583-588.

[168] Burns, J. M., Gallo, R. C., DeVico, A. L., and Lewis, G. K. 1998. A new monoclonal antibody, mAb 4A12, identifies a role for the glycosaminoglycan (GAG) binding domain of RANTES in the antiviral effect against HIV-1 and intracellular Ca2+ signaling. J Exp Med 188:1917-1927.

[169] Vujcic, L. K., and Quinnan, G. V., Jr. 1995. Preparation and characterization of human HIV type 1 neutralizing reference sera. AIDS Res. Hum. Retroviruses 11:783-787.

[170] Daar, E. S., Li, X. L., Moudgil, T., and Ho, D. D. 1990. High concentrations of recombinant soluble CD4 are required to neutralize primary human immunodeficiency virus type 1 isolates. Proc. Natl. Acad. Sci. U.S.A. 87:6574-6578.

[171] Connor, R. I., Sheridan, K. E., Ceradini, D., Choe, S., and Landau, N. R. 1997. Change in coreceptor use correlates with disease progression in HIV-1-infected individuals. J. Exp. Med. 185:621-628.

[172] Connor, R. I., Mohri, H., Cao, Y., and Ho, D. D. 1993. Increased viral burden and cytopathicity correlate temporally with CD4+ T-lymphocyte decline and clinical progression in human immunodeficiency virus type 1-infected individuals. J. Virol. 67:1772-1777.

[173] Werdelin, O., Meldal, M., and Jensen, T. 2002. Processing of glycans on glycoprotein and glycopeptide antigens in antigen-presenting cells. Proc Natl Acad Sci USA 99:9611-9613.

[174] Zhou, D., Mattner, J., Cantu, C., 3rd, Schrantz, N., Yin, N., Gao, Y., Sagiv, Y., Hudspeth, K., Wu, Y. P., Yamashita, T., Teneberg, S., Wang, D., Proia, R. L., Levery, S. B., Savage, P. B., Teyton, L., and Bendelac, A. 2004. Lysosomal glycosphingolipid recognition by NKT cells. Science 306:1786-1789.

What is claimed is:

1. A method of simultaneously adding two homogeneous oligosaccharide N-glycans adjacent to a V3 domain of HIV gp120, the method comprising:

providing a precursor peptide comprising the V3 domain of HIV gp120 and two Asn amino acid residues wherein the two Asn residues are positioned adjacent to two cysteine residues of the V3 domain and wherein each of the two Asn amino acid residues comprise a N-acetylglucosamine (GlcNAc) moiety and act as a GlcNAc-peptide acceptor; and conducting a transglycosylation reaction between an excess of a pre-assembled homogeneous oligosaccharide oxazoline and the two GlcNAc-peptide acceptors under the catalysis of Endo-A or Endo-M to generate two homogeneous oligosaccharide N-glycans positioned at the Asn amino acid residues adjacent to the V3 domain.

2. The method according to claim 1, wherein the oligosaccharide oxazoline is a di- or tetrasaccharide oxazoline.

3. The method according to claim 1, wherein the N-acetylglucosamine (GlcNAc) moiety is positioned on two Asn residues each adjacent to a cysteine residue of a sequence comprising amino acid residues of TSVEINCTRPNNNTRKRIRIQRG-PGRAFVTIGKIGNMRQAHCNISRA (SEQ ID NO 1); or ESVEINCRPNNNTRKSIHIGPGRAFYT-TGEIIGDIRQAHCNISRA (SEQ ID NO 2).

4. A method to synthesize a HIV glycoprotein comprising a V3 domain of gp120, the method comprising: synthesizing a peptide comprising the V3 domain of HIV gp 120 containing at least one N-acetylglucosamine (GlcNAc) moiety to form GlcNAc-peptide acceptor;

wherein the N-acetylglucosamine (GlcNAc) moiety is positioned at an Asn amino acid residue of the V3 domain; and transglycosylating a di- or tetrasaccharide oxazoline and the GlcNAc-peptide acceptor under the catalysis of the enzyme Endo-A to form the HIV glycoprotein including the V3 domain.

5. A method of simultaneously adding at least two pentasaccharide N-glycans to a glycopeptide comprising a V3 domain of HIV gp120, the method comprising:

providing a precursor peptide comprising TSVEINCTRP-NNNTRKRIRIQRGPGRAFVTIGKIGNM-RQAHCNISRA (SEQ ID NO 1) wherein two Asn residues, each adjacent to a cysteine residue comprise a GlcNAc moiety attached thereto, and conducting a transglycosylation reaction between an excess of tetrasaccharide oxazoline and the two GlcNAc moieties under the catalysis of Endo-A or Endo-M to generate two homogeneous core pentasaccharide N-glycans on the glycopeptide.

6. A method of making a synthetic glycopeptide comprising a HIV gp120 V3-domain, the method comprising:

adding at least one synthetic oligosaccharide oxazoline to a GlcNAc-containing peptide precursor, wherein the GlcNAc-containing peptide precursor comprises the HIV gp 120 V3 -domain;

attaching the at least one synthetic oligosaccharide oxazoline to at least one Asn residue comprising a GlcNAc moiety in the presence of an enzyme selected from the group consisting of Endo-A and Endo-M, wherein the one Asn residue comprising the GlcNAc moiety is within the amino acid sequence of the V3 -domain or adjacent thereof.

7. The method according to claim 6, wherein the enzyme is Endo-A.

8. The method according to claim 6, wherein the enzyme is Endo-M.

9. The method according to claim 6, wherein the synthetic oligosaccharide oxazoline comprises a di- or tetrasaccharide oxazoline.

10. The method according to claim 9, wherein the synthetic oligosaccharide oxazoline comprises a disaccharide oxazoline.

11. The method according to claim 9, wherein the synthetic oligosaccharide oxazoline comprises a tetrasaccharide oxazoline.

* * * * *

UNITED STATES PATENT AND TRADEMARK OFFICE

CERTIFICATE OF CORRECTION

PATENT NO. : 7,728,106 B2
APPLICATION NO. : 11/479701
DATED : June 1, 2010
INVENTOR(S) : Lai-Xi Wang It is certified that error appears in the above-identified patent and that said Letters Patent is hereby corrected as shown below:

In the Specifications:

Column 1, lines 18-19: "The United States Government has rights in this invention under Grant Nos. R21 AI051235 and R21 AI054354."

Should be: "This invention was made with government support under Grant Numbers AI051235 and AI054354 awarded by the National Institutes of Health. The government has certain rights in the invention."

Signed and Sealed this
Ninth Day of July, 2013

Teresa Stanek Rea
*Acting Director of the United States Patent and Trademark Office*

SEQUENCE LISTING

```
<160> NUMBER OF SEQ ID NOS: 2

<210> SEQ ID NO 1
<211> LENGTH: 47
<212> TYPE: PRT
<213> ORGANISM: Human immunodeficiency virus

<400> SEQUENCE: 1

Thr Ser Val Glu Ile Asn Cys Thr Arg Pro Asn Asn Asn Thr Arg Lys
1               5                   10                  15

Arg Ile Arg Ile Gln Arg Gly Pro Gly Arg Ala Phe Val Thr Ile Gly
            20                  25                  30

Lys Ile Gly Asn Met Arg Gln Ala His Cys Asn Ile Ser Arg Ala
        35                  40                  45


<210> SEQ ID NO 2
<211> LENGTH: 45
<212> TYPE: PRT
<213> ORGANISM: Human immunodeficiency virus

<400> SEQUENCE: 2

Glu Ser Val Glu Ile Asn Cys Arg Pro Asn Asn Asn Thr Arg Lys Ser
1               5                   10                  15
```

-continued

```
Ile His Ile Gly Pro Gly Arg Ala Phe Tyr Thr Thr Gly Glu Ile Ile
        20                  25                  30

Gly Asp Ile Arg Gln Ala His Cys Asn Ile Ser Arg Ala
    35                  40                  45
```